US007642350B2

(12) United States Patent
Pryde

(10) Patent No.: US 7,642,350 B2
(45) Date of Patent: Jan. 5, 2010

(54) PURINE DERIVATIVES

(75) Inventor: David Pryde, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 577 days.

(21) Appl. No.: 11/417,982

(22) Filed: May 3, 2006

(65) Prior Publication Data

US 2006/0264448 A1    Nov. 23, 2006

Related U.S. Application Data

(60) Provisional application No. 60/678,054, filed on May 4, 2005.

(51) Int. Cl.
C07D 473/34 (2006.01)
A61K 31/522 (2006.01)
A61P 31/20 (2006.01)
A61P 31/14 (2006.01)

(52) U.S. Cl. .................. 544/61; 544/118; 544/276; 544/277

(58) Field of Classification Search .............. 544/61, 544/118, 276; 514/228.5, 234.2, 263.2, 263.22, 514/263.23, 263.37
See application file for complete search history.

(56) References Cited

U.S. PATENT DOCUMENTS

| 7,439,359 | B2 * | 10/2008 | Chiosis et al. | 544/277 |
| 2005/0054590 | A1 | 3/2005 | Averett | |
| 2006/0052403 | A1 | 3/2006 | Isobe et al. | |
| 2009/0047249 | A1 * | 2/2009 | Graupe et al. | 544/276 |
| 2009/0082332 | A1 * | 3/2009 | Abbot et al. | 544/276 |

FOREIGN PATENT DOCUMENTS

| EP | 1 035 123 | 8/2003 |
| EP | 1 386 923 | 2/2004 |
| EP | 0 882 727 | 12/2004 |
| EP | 1 550 662 | 6/2005 |
| EP | 1 043 021 | 5/2006 |
| WO | WO 91/11172 | 8/1991 |
| WO | WO 94/02518 | 2/1994 |
| WO | WO 98/55148 | 12/1998 |
| WO | WO 00/35298 | 6/2000 |
| WO | WO 2004/029054 | 4/2004 |
| WO | WO 2004/087049 | 10/2004 |
| WO | 2005/025583 | 3/2005 |
| WO | WO 2008047201 A2 * | 4/2008 |

OTHER PUBLICATIONS

Isobe, Bioorganic & Medicinal Chemistry (2003), 11(17), 3641-3647.*
PCT International Search Report, PCT/IB2006/001181.
Akira, S., et al., "Toll-Like Receptors," *Annual Rev. Immunol.*, 2003, 335-376, vol. 21.

Almarsson, O., et al., "Crystal Engineering Of The Composition Of Pharmaceutical Phases. Do Pharmaceutical Co-Crystals Represent A New Path To Improved Medicines?" *Chem. Commun.*, 2004, 1889-1896, vol. 17.
Chiosis, G., et al., "Development Of A Purine-Scaffold Novel Class Of Hsp90 Binders That Inhibit The Proliferation Of Cancer Cells And Induce The Degradation Of Her2 Tyrosine Kinase," *Bioorganic & Medicinal Chemistry*, 2002, 3555-3564, vol. 10.
Dabbagh, K., et al., "Toll-Like Receptors And T-Helper-1/T-Helper-2 Responses," *Curr Opin Infect Dis*, 2003 199-204, vol. 16.
Finnin, et al., "Transdermal Penetration Enhancers: Applications, Limitations, And Potential," Journal of Pharmaceutical Sciences, 1999, 955-958, vol. 88, No. 10.
Haleblian, J., "Characterization Of Habits And Crystalline Modification Of Solids And Their Pharmaceutical Applications," *Journal of Pharmaceutical Sciences*, 1975, 1269-1288, vol. 64, No. 8.
Harada, H., et al., "2-Alkynyl-8-Arylladenines Possessing An Amide Moiety: Their Synthesis And Structure-Activity Relationships Of Effects On Hepatic Glucose Production Induced Via Agonism Of The $A_{2B}$ Adenosine Receptor," *Bioorganic & Medicinal Chemistry*, 2001, 2709-2726, vol. 9.
Hirota, K., et al., "Efficient Synthesis Of 2,9-Disubstituted 8-Hydroxyadenine Derivatives," *Org. BioMol. Chem.*, 2003, 1354-1365, vol. 1.

(Continued)

*Primary Examiner*—Mark L Berch
(74) *Attorney, Agent, or Firm*—Keith D. Hutchinson; John H. Engelmann; Lucy X. Yang

(57) ABSTRACT

This invention relates to purine derivatives, to processes for their preparation, to compositions containing them and to their use.

The present invention provides compounds of formula (I)

(I)

wherein $R_1$, $R_2$, $R_3$, $R_9$, $R_{9a}$ and Y are defined in the description.

More particularly, the present invention relates to the use of purine derivatives in the treatment of a variety of viral infections and immune or inflammatory disorders, including those in which the modulation, in particular agonism, of Toll-Like Receptors (TLRs) is implicated. Accordingly, the compounds of the invention are useful in the treatment of infectious disease such as Hepatitis (e.g. HCV, HBV), genetically related viral infections, inflammatory diseases such as asthma and arthritis, and cancer.

2 Claims, No Drawings

OTHER PUBLICATIONS

Hoffman, J., "The Immune Response Of *Drosophila*," *Nature*, 2003, 33-38, vol. 426.

Kurimoto, A., et al., "Synthesis And Structure-Activity Relationships Of 2-Amino-8-Hydroxyadenines As Orally Active Interferon Inducing Agents," *Bioorganic & Medicinal Chemistry*, 2003, 5501-5508, vol. 11.

Liang, A., et al., "Fast-Dissolving Intraoral Drug Delivery Systems," *Expert Opinion In Therapeutic Patents*, 2001, 981-986, vol. 11, No. 6.

Madding, G., et al., "Regioselective Syntheses of 2-Amino-4,5-dialkylthiophene-3-Carboxylates And Their Conversion To 3,4-Dihydro-4-0xothieno[2,3-*d*]Pyrimidine-2-Carboxylates," *J. Heterocyclic Chem.*, 1987, 581-587, vol. 24.

Rajappan, V., et al., "A Flexible Synthesis Of Carbanucleosides and 5'-nor-1'-Homo Carbanucleosides From A common Precursor," *Tetrahedron*, 2002, 9889-9895, vol. 58.

Temple, C., et al., "Preparation of 2,5-Diamino-4,6-Dichloropyrimidine," *J. Org. Chem.*, 1975, 3141-3142, vol. 40, No. 21.

Ulevitch, R., "Therapeutics Targeting The Innate Immune System," *Nature Reviews: Immunology*, 2004, 512-520, vol. 4.

Verma, R., et al., "Current Status Of Drug Delivery Technologies And Future Directions," *Pharmaceutical Technology On-Line*, 2001, 1-14, vol. 25, No. 2.

Yokomatsu, T., et al., "Stereoselective Reduction Of Cyclopropylalkaones Possessing A Difluoromethylenephosphonate Group At The Ring: Application To Stereoselective Synthesis Of Novel Cyclopropane Nucleotide Analogues," *Tetrahedron*, 2000, 7099-7108, vol. 56.

\* cited by examiner

PURINE DERIVATIVES

PRIORITY CLAIM

This application claims the benefit of U.S. Provisional Application No. 60/678,054, filed May 4, 2005, and incorporates said application herein in its entirety.

BACKGROUND OF THE INVENTION

This invention relates to purine derivatives, to processes for their preparation, to compositions containing them and to their use.

More particularly, the present invention relates to the use of purine derivatives in the treatment of a variety of viral infections and immune or inflammatory disorders, including those in which the modulation, in particular agonism, of Toll-Like Receptors (TLRs) is implicated. Accordingly, the compounds of the invention are useful in the treatment of infectious disease such as Hepatitis (e.g. HCV, HBV), genetically related viral infections, inflammatory diseases such as asthma and arthritis, and cancer.

Toll-Like Receptors are primary transmembrane proteins characterized by an extracellular leucine-rich domain and a cytoplasmic tail that contains a conserved region named the Toll/IL-1 receptor (TIR) domain. They are expressed predominantly on immune cells (for example dendritic cells, T lymphocytes, macrophages, monocytes and natural killer cells), which serve as a key part of the innate immune system. They are a group of pattern recognition receptors which bind to pathogen-associated molecular patterns [for reviews, see for example, Ulevitch, R. J., *Nature Reviews: Immunology,* 4, 512-520, 2004 and Akira, S., Takeda, K., and Kaisho, T., *Annual Rev. Immunol.,* 21, 335-376, 2003]. Their name derives from sequence homology to the *Drosophila melanogaster* gene Toll, which was found in fruit flies to play a key role in protecting the fly from fungal infections [Hoffmann, J. A., *Nature,* 426, 33-38, 2003]. There are 11 TLRs which have been identified in mammalian systems, and other non-mammalian TLRs have been found in other vertebrates. All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-α, interleukins, MIP-1 and MCP-1 which contribute to the killing and clearance of the pathogenic invasion. By activating TLRs with small molecule agonists, it should be possible to induce or stimulate immune cells to mount an immune response.

Purine derivatives are disclosed in EP-A-0 882 727, EP-A-1 035 123, EP-A-1 043 021, EP-A-1 386 923 and WO 2004/029054. WO 2004/087049 and US 2005/054590 disclose modulators of TLR7.

There is a need for further modulators, especially agonists, of the activity of the $TLR_7$ receptor, and preferably agonists which are more selective, have a more rapid onset of action, are more potent, are better absorbed, are more stable, are more resistant to metabolism, have a reduced 'food effect', have an improved safety profile or have other more desirable properties (e.g. with respect to solubility or hygroscopicity) than the compounds of the prior art.

SUMMARY OF THE INVENTION

It has now been found that C2-amido purine derivatives are potent immune response modifiers which act selectively through modulation, especially agonism, of the TLR7 receptor. Accordingly, the invention provides a compound of formula (I):

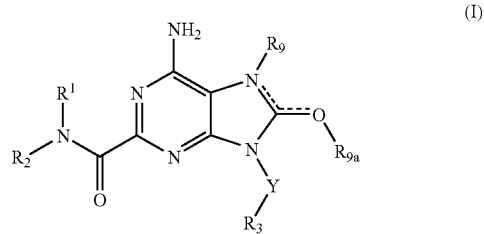

a tautomer thereof or a pharmaceutically acceptable salt, solvate or polymorph of said compound or tautomer, wherein:
$R_1$ and $R_2$ are each independently H; $C_{1-6}$ alkyl; $C_{3-7}$ cycloalkyl; $C_{1-6}$ alkyl substituted by 1 to 3 $C_{3-7}$ cycloalkyl(s), a phenyl, a naphthyl or a heterocycle; $C_{3-7}$ cycloalkyl substituted by $C_{1-6}$ alkyl; $S(O)_nR_8$; or heterocycle; or $R_1$ and $R_2$, taken together with the nitrogen atom to which they are bonded, form a heterocycle; wherein in each instance said alkyl, cycloalkyl, phenyl, naphthyl and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $S(O)_nNR_4R_5$, $CONR_4R_5$ and $NR_4COR_5$;

$R_3$ is $C_{1-6}$ alkyl; $C_{3-7}$ cycloalkyl; phenyl; naphthyl; or heterocycle; wherein said alkyl, cycloalkyl, phenyl, naphthyl and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $S(O)_nNR_4R_5$, $CONR_4R_5$ and $NR_4COR_5$;

$R_4$ and $R_5$ are each independently H; $C_{1-6}$ alkyl; $C_{3-7}$ cycloalkyl; $C_{2-6}$ alkenyl; or $C_{2-6}$ alkynyl; or $R_4$ and $R_5$, when bound to the same nitrogen atom, form a heterocycle; wherein said alkyl, cycloalkyl and heterocycle are optionally substituted by 1 to 3 atoms or groups selected from phenyl, $OR_6$, $NR_6R_7$, $S(O)_nR_6$, $S(O)_nNR_6R_7$ and $NR_6COR_7$;

$R_6$ and $R_7$ are independently H; $C_{1-6}$ alkyl; or $C_{1-6}$ alkyl substituted by $C_{3-7}$ cycloalkyl; or $R_6$ and $R_7$, when bound to the same nitrogen atom, form a heterocycle;

$R_8$ is H; $C_{1-6}$ alkyl; $C_{3-7}$ cycloalkyl; phenyl; naphthyl; or heterocycle; wherein said alkyl, cycloalkyl, phenyl, naphthyl and heterocycle are optionally substituted by 1 to 3 atoms or groups selected from oxo, halogen, $CF_3$, CN, phenyl, $R_4$, $OR_4$, $NR_4R_5$, $COR_4$, $CO_2R_4$, $S(O)_nR_4$, $S(O)_nNR_4R_5$, $CONR_4R_5$ and $NR_4COR_5$;

$R_9$ is $R_{10}$, $COR_{10}$, $CO_2R_{10}$, or $CONR_{10}R_{11}$, and $R_{9a}$ is absent; or $R_{9a}$ is $R_{10}$, $COR_{10}$, $CO_2R_{10}$, or $CONR_{10}R_{11}$, and $R_9$ is absent;

$R_{10}$ and $R_{11}$ are each independently H; $C_{1-6}$ alkyl; $C_{3-7}$ cycloalkyl; $C_{1-6}$ alkyl substituted by 1 to 3 $C_{3-7}$ cycloalkyl(s), a phenyl, a naphthyl or a heterocycle; $C_{3-7}$ cycloalkyl substituted by $C_{1-6}$ alkyl; phenyl; naphthyl; or heterocycle; or $R_{10}$ and $R_{11}$, taken together with the nitrogen atom to which they are bonded, form a heterocycle; wherein in each instance said alkyl, cycloalkyl, phenyl, naphthyl and heterocycle are optionally substituted by 1 to 3 atoms or groups selected from oxo, halogen, $CF_3$, CN, $R_{12}$, $OR_{12}$, $NR_{12}R_{13}$, $COR_{12}$, $CO_2R_{12}$, $S(O)_pR_{12}$, $S(O)_pNR_{12}R_{13}$, $CONR_{12}R_{13}$ and $NR_{12}COR_{13}$;

$R_{12}$ and $R_{13}$ are independently H; $C_{1-6}$ alkyl; or $C_{1-6}$ alkyl substituted by $C_{3-7}$ cycloalkyl; or $R_{12}$ and $R_{13}$, when bound to the same nitrogen atom, form a heterocycle;

Y is a direct bond or a $C_{1-4}$ alkylene;

n is 0, 1 or 2;

p is 0, 1 or 2;

with the proviso that when Y is methylene and $R_3$ is phenyl, then $R_1$ and $R_2$ are not simultaneously methyl.

The term "alkyl" refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, n-pentyl, isoamyl, n-hexyl.

The term "alkenyl" refers to an alkyl as defined above, consisting of at least two carbon atoms and at least one carbon-carbon double bond.

The term "alkynyl" refers to an alkyl as defined above, consisting of at least two carbon atoms and at least one carbon-carbon triple bond.

The term "cycloalkyl" refers to a carbocyclic ring containing the specified number of carbon atoms. Examples of carbocyclic rings include cyclopropyl, cyclobutyl, cyclopentyl, cyclohexyl and cycloheptyl.

The term "halogen" refers to fluorine, chlorine, bromine or iodine.

The term "heterocycle" refers to (i) 4- to 12-membered saturated or partially unsaturated heterocyclic group in which one to three carbon atoms are replaced by heteroatoms selected from N, O and S, which group is monocyclic or polycyclic (e.g. bicyclic or tricyclic), and is optionally fused, bridged or spiranic, and (ii) 5- to 12 membered aromatic heterocyclic group containing one to three heteroatoms selected from N, O and S, which group is monocyclic or polycyclic (e.g. bicyclic or tricyclic), and is optionally fused, bridged or spiranic, and which group may be optionally benzofused if monocyclic. When the heterocycle contains one or more nitrogen atoms, N-oxides are included within the scope of the invention.

Examples of saturated or partially unsaturated heterocyclic groups include, but are not limited to, azetidine, pyrrolidine, thiazolidine, tetrahydrofuran, piperidine, piperazine, morpholine, thiomorpholine, tetrahydropyrane, tetrahydrothiopyrane, dioxane, dioxole, diazepine, diazepane, azabicycloheptane, diazobicycloheptane, azabicycloheptene, azabicyclooctane, diazobicyclooctane, oxaazabicyclooctane, azaadamantane, dihydroisoindole, octahydropyrrolopyrazine, octahydropyrrolopyrrole, decahydropyrrolopyrrolizine, tetrahydroisoxazolopyridine, tetrahydroisoxazolopyridine, tetrahydroimidazopyridine, tetrahydropyrazolopyridine.

Examples of aromatic heterocyclic groups include, but are not limited to, thiophene, pyrrole, imidazole, triazole, tetrazole, pyridine, pyrazole, pyrazine, pyrimidine, pyridazine, thiadiazine, oxazole, thiazole, isoxazole, isothiazole, isoindole, pyrrolopyrazine, isoxazolopyridine, imidazopyridine, pyrazolopyridine.

In one embodiment, $R_1$ is H; $C_{1-4}$ alkyl; $C_{4-6}$ cycloalkyl; $C_{1-4}$ alkyl substituted by 1 to 3 $C_{3-7}$ cycloalkyl(s), a phenyl, or a heterocycle; $C_{4-6}$ cycloalkyl substituted by $C_{1-4}$ alkyl; $S(O)_n$ $R_8$; or heterocycle; wherein in each instance said alkyl, cycloalkyl, phenyl, and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$.

In a further embodiment, $R_1$ is H; $C_{1-4}$ alkyl; $C_{4-6}$ cycloalkyl; $C_{1-3}$ alkyl substituted by 1 to 3 $C_{3-7}$ cycloalkyl(s); $C_{1-2}$ alkyl substituted by a phenyl; $C_{1-4}$ alkyl substituted by a heterocycle; $C_{4-6}$ cycloalkyl substituted by $C_{1-4}$ alkyl; $S(O)_2$ $R_8$; or heterocycle; wherein in each instance said alkyl, cycloalkyl, phenyl, and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$.

In a further embodiment, $R_1$ is H; $C_{1-4}$ alkyl; $C_{4-6}$ cycloalkyl; $C_{1-2}$ alkyl substituted by 1 to 2 $C_{3-5}$ cycloalkyl(s); $C_{1-3}$ alkyl substituted by a phenyl; $C_{1-4}$ alkyl substituted by a heterocycle; $C_{4-6}$ cycloalkyl substituted by $C_{1-3}$ alkyl; $S(O)_2$ $R_8$; or heterocycle; wherein in each instance said alkyl, cycloalkyl, phenyl, and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$; and wherein in each instance said heterocycle is selected from pyrrolidine, piperidine, piperazine, morpholine, tetrahydropyran, tetrahydrofuran, dioxane, pyridine, pyrimidine, pyrazine, pyrazole, imidazole, isoxazole and thiazole.

In one embodiment, $R_1$ is H; $C_{1-4}$ alkyl; $C_{1-4}$ alkyl substituted by $OR_4$ or $C_{3-7}$ cycloalkyl. In a further embodiment, $R_1$ is H, methyl, ethyl, propyl, 2-hydroxyethyl, 2-methoxypropyl, cyclopropylmethyl.

In one embodiment, $R_1$ is $C_{1-2}$ alkyl substituted by 1 to 2 $C_{3-5}$ cycloalkyl(s); $C_1$ alkyl substituted by phenyl; $SO_2R_8$; or heterocycle; wherein in each instance said alkyl, cycloalkyl, phenyl, and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$.

In a further embodiment, $R_1$ is $C_{1-2}$ alkyl substituted by 1 to 2 $C_{3-5}$ cycloalkyl(s); wherein said alkyl and cycloalkyl are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$. In yet a further embodiment, $R_1$ is $C_{1-2}$ alkyl substituted by 1 to 2 $C_{3-5}$ cycloalkyl(s).

In a further embodiment, $R_1$ is $C_1$ alkyl substituted by phenyl.

In a further embodiment, $R_1$ is $SO_2R_8$.

In a further embodiment, $R_1$ is heterocycle optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$. In a yet a further embodiment, $R_1$ is heterocycle optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $CONR_4R_5$ and $NR_4COR_5$; wherein said heterocycle is selected from pyrrolidine, piperidine, piperazine, morpholine, tetrahydropyran, tetrahydrofuran, dioxane, pyridine, pyrimidine, pyrazine, pyrazole, imidazole, isoxazole and thiazole.

In one embodiment, $R_2$ is H, or $C_{1-4}$ alkyl optionally substituted by $OR_4$. In a further embodiment, $R_2$ is H or $C_{1-4}$ alkyl. In yet a further embodiment, $R_2$ is H.

In one embodiment, $R_1$ and $R_2$, taken together with the nitrogen atom to which they are bonded, form a heterocycle; wherein said heterocycle is optionally substituted by 1 to 3 atoms or groups selected from oxo, halogen, $CF_3$, CN, $R_4$, $OR_4$, $NR_4R_5$, $COR_4$, $CO_2R_4$, $CONR_4R_5$ and $NR_4COR_5$. In a further embodiment, $R_1$ and $R_2$, taken together with the nitrogen atom to which they are bonded, form a heterocycle optionally substituted by oxo, halogen, $CF_3$, CN, $R_4$, $OR_4$.

In a further embodiment, $R_1$ and $R_2$, taken together with the nitrogen atom to which they are bonded, form a heterocycle; wherein said heterocycle is optionally substituted by 1 to 3 atoms or groups selected from oxo, halogen, $CF_3$, CN, $R_4$, $OR_4$, $NR_4R_5$, $COR_4$, $CO_2R_4$, $CONR_4R_5$ and $NR_4COR_5$, and wherein said heterocycle is selected from azetidine, pyrrolidine, piperidine, piperazine, morpholine, thiomorpholine, diazepane, thiazolidine, diazobicyclooctane, diazobicycloheptane, octahydropyrrolopyrrole, decahydropyrrolopyrrolizine, octahydropyrrolopyrazine, and tetrahydroisoxazolopyridine.

In a further embodiment, $R_1$ and $R_2$, taken together with the nitrogen to which they are bonded, form an azetidine, pyrrolidine, piperidine, piperazine, morpholine or thiomorpholine ring, said ring being optionally substituted by $C_{1-4}$ alkyl or $C_{1-4}$alkoxy$C_{1-4}$alkyl.

In one embodiment, $R_3$ is $C_{1-4}$ alkyl or phenyl; wherein said alkyl and phenyl are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $S(O)_nNR_4R_5$, $CONR_4R_5$ and $NR_4COR_4$. In a further embodiment, $R_3$ is phenyl optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $S(O)_nNR_4R_5$, $CONR_4R_5$ and $NR_4COR_4$, in yet a further embodiment, $R_3$ is phenyl substituted by halogen or $CF_3$. In yet a further embodiment, $R_3$ is phenyl. In a further embodiment, $R_3$ is $C_{1-4}$ alkyl optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $S(O)_nNR_4R_5$, $CONR_4R_5$ and $NR_4COR_4$. In yet a further embodiment, $R_3$ is $C_{1-3}$ alkyl optionally substituted by $OR_4$. In yet a further embodiment, $R_3$ is methoxymethyl.

In one embodiment, $R_4$ is H; $C_{1-4}$ alkyl; $C_{3-6}$ cycloalkyl; or $C_{2-4}$ alkynyl; wherein said alkyl and cycloalkyl are optionally substituted by 1 to 3 atoms or groups selected from $OR_6$, $NR_6R_7$, $S(O)_nR_6$, $S(O)_nNR_6R_7$ and $NR_6COR_7$. In a further embodiment, $R_4$ is H; $C_{1-4}$ alkyl; $C_{3-6}$ cycloalkyl; or $C_{2-4}$ alkynyl; wherein said alkyl is optionally substituted by 1 to 3 atoms or groups selected from $OR_6$. In yet a further embodiment, $R_4$ is H or $C_{1-4}$ alkyl. In yet a further embodiment, $R_4$ is H or methyl.

In one embodiment, $R_5$ is H or $C_{1-4}$ alkyl.

In one embodiment, $R_4$ and $R_5$, when bound to the same nitrogen atom, form a heterocycle; wherein said heterocycle is optionally substituted by 1 to 3 atoms or groups selected from phenyl, $OR_6$, $NR_6R_7$, $S(O)_nR_6$, $S(O)_nNR_6R_7$ and $NR_6COR_7$. In a further embodiment, $R_4$ and $R_5$, when bound to the same nitrogen atom, form pyrrolidine or pyrazole; wherein said pyrrolidine or pyrazole are optionally substituted by 1 to 3 atoms or groups selected from phenyl, $OR_6$, $NR_6R_7$, $S(O)_nR_6$, $S(O)_nNR_6R_7$ and $NR_6COR_7$.

In one embodiment, $R_6$ is H or $C_{1-4}$ alkyl. In a further embodiment, $R_6$ is H or methyl.

In one embodiment, $R_7$ is H or $C_{1-4}$ alkyl. In a further embodiment, $R_7$ is H.

In one embodiment, $R_8$ is $C_{1-6}$ alkyl; $C_{3-7}$ cycloalkyl; or phenyl; wherein said alkyl, cycloalkyl and phenyl are optionally substituted by 1 to 3 atoms or groups selected from oxo, halogen, $CF_3$, CN, phenyl, $R_4$, $OR_4$, $NR_4R_5$, $COR_4$, $CO_2R_4$, $S(O)_nR_4$, $S(O)_nNR_4R_5$, $CONR_4R_5$ and $NR_4COR_5$. In a further embodiment, $R_8$ is $C_{1-4}$ alkyl; $C_{4-6}$ cycloalkyl; or phenyl; wherein said alkyl, cycloalkyl, and phenyl are optionally substituted by 1 to 3 atoms or groups selected from halogen, phenyl, or $R_4$.

In one embodiment, the present invention provides compounds of formula (I) wherein $R_9$ is $R_{10}$, $COR_{10}$, $CO_2R_{10}$, or $CONR_{10}R_{11}$, and $R_{9a}$ is absent, to give compounds of formula (IA)

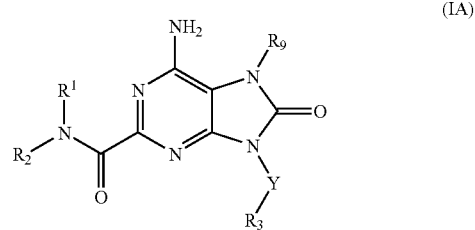

(IA)

or a pharmaceutically acceptable salt, solvate or polymorph thereof, wherein:

$R_1$, $R_2$, $R_3$, and Y are as defined hereinabove with respect to a compound of formula (I), including all embodiments, and combinations of particular embodiments thereof;

In another embodiment, the present invention provides compounds of formula (I) wherein $R_{9a}$ is $R_{10}$, $COR_{10}$, $CO_2R_{10}$, or $CONR_{10}R_{11}$, and $R_9$ is absent, to give compounds of formula (IB)

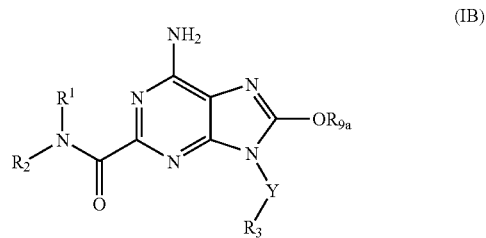

(IB)

or a pharmaceutically acceptable salt, solvate or polymorph thereof, wherein:

$R_1$, $R_2$, $R_3$ and Y are as defined hereinabove with respect to a compound of formula (I), including all embodiments, and combinations of particular embodiments thereof;

In one embodiment, $R_9$ is H.

In another embodiment, $R_{9a}$ is H.

In one embodiment, $R_{10}$ is $C_{1-3}$ alkyl; $C_{1-3}$ alkyl substituted by a phenyl; phenyl; or heterocycle; wherein in each instance said alkyl, phenyl and heterocycle are optionally substituted by 1 to 3 atoms or groups selected from oxo, halogen, $CF_3$, CN, $R_{12}$, $OR_{12}$, $NR_{12}R_{13}$, $COR_{12}$, $CO_2R_{12}$, $S(O)_pR_{12}$, $S(O)_pNR_{12}R_{13}$, $CONR_{12}R_{13}$ and $NR_{12}COR_{13}$.

In a further embodiment, $R_{10}$ is $C_{1-4}$ alkyl; $C_1$ alkyl substituted by a phenyl; phenyl; or heterocycle; wherein in each instance said alkyl, phenyl and heterocycle are optionally substituted by 1 to 2 atoms or groups selected from oxo, $R_{12}$ and and $OR_{12}$.

In one embodiment, $R_{11}$, is H or $C_{1-4}$ alkyl.

In one embodiment, $R_{10}$ and $R_{11}$, taken together with the nitrogen atom to which they are bonded, form a heterocycle; wherein said heterocycle is optionally substituted by 1 to 3 atoms or groups selected from oxo, halogen, $CF_3$, CN, $R_{12}$, $OR_{12}$, $NR_{12}R_{13}$, $COR_{12}$, $CO_2R_{12}$, $S(O)_pR_{12}$, $S(O)_pNR_{12}R_{13}$, $CONR_{12}R_{13}$ and $NR_{12}COR_{13}$.

In one embodiment, $R_{10}$ and $R_{11}$, taken together with the nitrogen atom to which they are bonded, form pyrrolidine, piperidine or morpholine; wherein said pyrrolidine, piperidine and morpholine are optionally substituted by 1 to 3 atoms or groups selected from oxo, halogen, $CF_3$, CN, $R_{12}$, $OR_{12}$, $NR_{12}R_{13}$, $COR_{12}$, $CO_2R_{12}$, $S(O)_pR_{12}$, $S(O)_pNR_{12}R_{13}$, $CONR_{12}R_{13}$ and $NR_{12}COR_{13}$.

In one embodiment, $R_{12}$ is H or $C_{1-4}$ alkyl. In a further embodiment, $R_{12}$ is H or methyl.

In one embodiment, $R_{13}$ is H or $C_{1-4}$ alkyl.

In one embodiment, Y is a $C_{1-4}$ alkylene. In a further embodiment, Y is methylene.

It is to be understood that the invention covers all combinations of particular embodiments of the invention as described hereinabove, consistent with the definition of the compounds of formula (I).

DETAILED DESCRIPTION OF THE INVENTION

The compounds of the invention include the compounds of formula (I) and tautomers thereof, and pharmaceutically acceptable salts, solvates or polymorphs of said compounds or tautomers In a further embodiment, the compounds of the invention are the compounds of formula (I) and tautomers thereof, and pharmaceutically acceptable salts and solvates of said compounds or tautomers, in particular the compounds of formula (I).

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as—$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4$^{th}$ Edition (Edward Arnold, 1970), incorporated herein by reference.

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Sys-* tems, Vol. 14, ACS Symposium Series (T. Higuchi and W. Stella) and *Bioreversible Carriers in Drug Design*, Pergamon Press, 1987 (Ed. E. B. Roche, American Pharmaceutical Association), both incorporated herein by reference.

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), incorporated herein by reference.

Some examples of prodrugs in accordance with the invention include (i) where the compound of formula I contains a carboxylic acid functionality, an ester thereof, for example, a compound wherein the hydrogen of the carboxylic acid functionality of the compound of formula (I) is replaced by $(C_1-C_8)$alkyl; and (ii) where the compound of formula (I) contains a primary or secondary amino functionality, an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references. Moreover, certain compounds of formula (I) may themselves act as prodrugs of other compounds of formula (I).

Specifically, compounds of the present invention of formula (I) wherein $R^9$ is as herein defined, other than H, and $R^{9a}$ is absent (i.e compounds of formula (IA)), may be converted into compounds of formula (I) wherein $R^9$ is H and $R^{9a}$ is absent via metabolic actions or solvolysis. Additionaly, compounds of the present invention of formula (I) wherein $R^9$ is absent and $R^{9a}$ is as herein defined, other than H (i.e compounds of formula (IB)), may be converted into compounds of formula (I) wherein $R^9$ is absent and $R^{9a}$ is H via metabolic actions or solvolysis.

Also included within the scope of the invention are metabolites of compounds of formula (I), that is, compounds formed in vivo upon administration of the drug. Some examples of metabolites in accordance with the invention include:

(i) where the compound of formula (I) contains a methyl group, an hydroxymethyl derivative thereof (—$CH_3$->—$CH_2OH$):

(ii) where the compound of formula (I) contains an alkoxy group, an hydroxy derivative thereof (—OR->—OH);

(iii) where the compound of formula (I) contains a tertiary amino group, a secondary amino derivative thereof (—$NR^1R^2$->—$NHR^1$ or —$NHR^2$);

(iv) where the compound of formula (I) contains a secondary amino group, a primary derivative thereof (—$NHR^1$->—$NH_2$);

(v) where the compound of formula (I) contains a phenyl moiety, a phenol derivative thereof (—Ph->-PhOH); and (vi) where the compound of formula (I) contains an amide group, a carboxylic acid derivative thereof (—$CONH_2$->COOH).

The compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

In particular, a compound of formula (IA) wherein $R_9$ is H is the tautomer of the compound of formula (IB) wherein $R_{9a}$ is H:

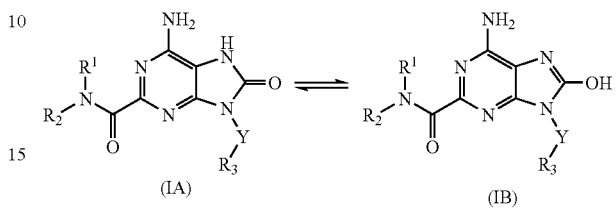

(IA)      (IB)

Included within the scope of the present invention are all stereoisomers, geometric isomers and tautomeric forms of the compounds of formula (I) and pharmaceutically acceptable salts, solvates or derivatives thereof (as hereinabove defined), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

The present invention also includes all pharmaceutically acceptable isotopically-labelled compounds of formula (I) wherein one or more atoms are replaced by atoms having the same atomic number, but an atomic mass or mass number different from the atomic mass or mass number which predominates in nature.

Representative compounds of formula (I) include the compounds of Examples 1, 2, 4, 5, 6, 33, 132, 142, 222, 226, 227, 229, 244, 250; and pharmaceutically acceptable salts, solvates or derivatives thereof.

In the general processes, and schemes, that follow: AcOH is acetic acid; DCM is dichloromethane; THF is tetrahydrofuran; DEAD is diethylazodicarboxylate; DIAD is diisopropylazodicarboxylate, WSCDI is 1-(3-dimethylaminopropyl)-3-ethylcarbodiimide hydrochloride; DCC is N,N'-dicyclohexylcarbodiimide; HOAT is 1-hydroxy-7-azabenzotriazole; HOBt is 1-hydroxybenzotriazole hydrate; HBTU is O-benzotriazol-1-yl-N,N,N',N'-tetramethyluronium hexafluorophosphate; PyBrOP is bromo-tris-pyrrolidino-phosphonium hexafluorophosphate; BOP is benzotriazol-1-yl-oxy-tris(dimethylamino)phosphonium hexafluorophosphate; CDI is 1,1'-carbonyldiimidazole; T3P is thymidine-3'-phosphate.

The compounds of formula (I) may be prepared by any process used for preparing analogous compounds.

The compounds of formula (I) wherein $R_9$ is H and $R_{9a}$ is absent, or $R_{9a}$ is H and $R_9$ is absent, may be prepared as depicted in Scheme 1, wherein $R_1$ to $R_3$ and Y are as defined above, except that Y is other than a single bond when $R_3$ is phenyl, naphthyl or heterocycle.

Scheme 1

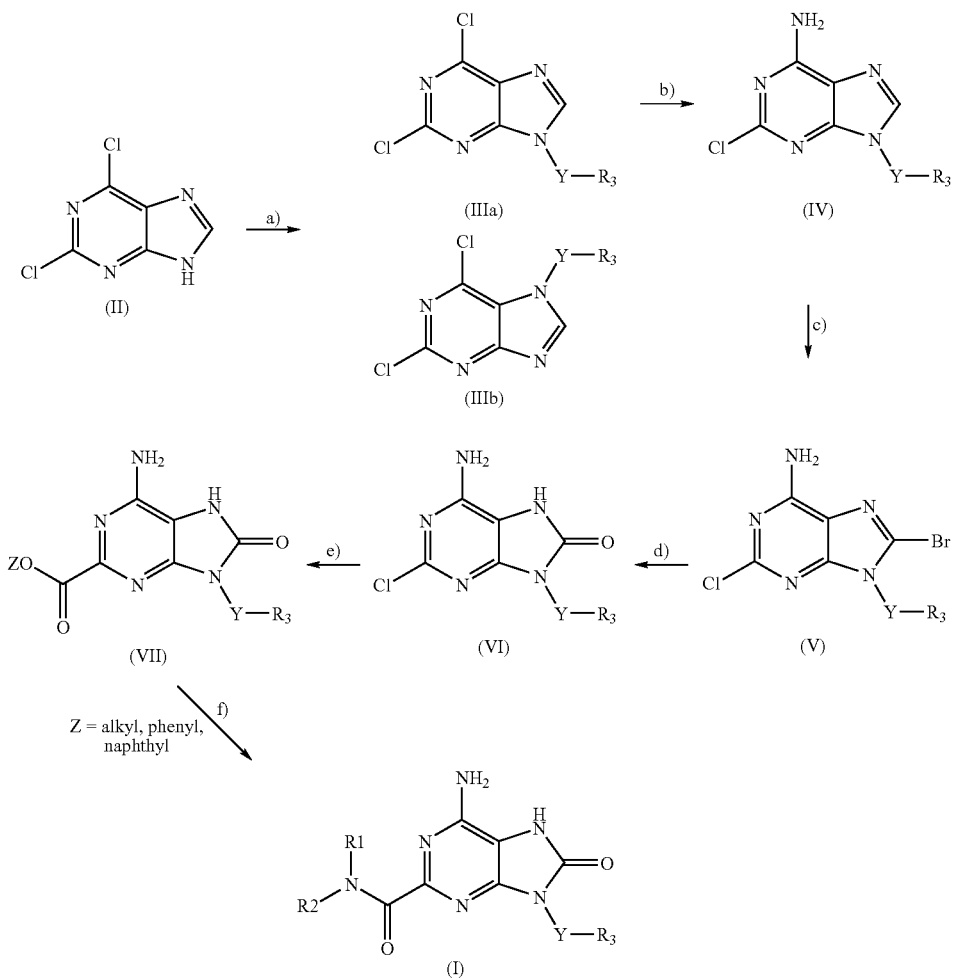

Z = alkyl, phenyl, naphthyl

The above synthesis of intermediate chloropurine (VI) [steps a)-e)] is based on a modification of the route described in *BioOrg. Med. Chem. Letts.,* 2003, 11, 5501-5508, incorporated herein by reference.

a) Commercially available dichloropurine (II) can be alkylated with an alkyl group bearing an appropriate leaving group (e.g halogen or sulfonate ester) to give typically a mixture of the N7 and N9 alkylated purines (IIIa) and (IIIb). These can be separated by recrystallisation from a suitable solvent such as ethanol or methanol or by silica gel chromatography. Alternatively, reaction of (II) with a primary or secondary alcohol in the presence of a suitable azodicarboxylate (DEAD or DIAD) and an alkyl or aryl phosphine (e.g. $PPh_3$ or $PBu_3$) in a suitable solvent (e.g. THF) using the method of *Tetrahedron,* 2000, 56, 7099-7108 and *Tetrahedron,* 2002, 58, 9889-9895 (both incorporated herein by reference) will yield predominantly the alkylated N9 purine (IIIa).

b)-c) Treatment of (IIIa) with ammonia gas in a suitable solvent such as water or ethanol in a pressurised steel reaction vessel can provide the aminopurine (IV), which can be halogenated with a suitable halogen source, typically $Br_2$, in a suitable solvent such as AcOH, carbon tetrachloride or DCM to give the 8-bromopurine (V).

d) Bromopurine (V) can then be hydrolysed under either acidic or basic conditions, typically with hydrochloric acid, in a suitable solvent such as butanol, to give the 8-oxo purine (VI).

e) The 8-oxo purine (VI) can then be carbonylated under a CO atmosphere, typically 50-200 psi (345-1379 kPa), in a suitable solvent, e.g. an alcohol ZOH, such as ethanol, in the presence of a suitable palladium catalyst, such as $PdCl_2$, $Pd(PPh_3)_4$ or $Pd(dppf)_2Cl_2$, and a base such as sodium or potassium carbonate to give the purine ester (VII).

f) The ester (VII) is used as a starting material for synthesis of amide (I) by heating with an appropriate amine $HNR_1R_2$, either neat or in a suitable solvent such as a lower alcohol (e.g. ethanol, propanol, butanol), optionally in a pressurised reaction vessel. Evaporation of the excess amine and/or solvent under reduced pressure provides the amide (I) which can optionally be further purified by recrystallisation from a suitable solvent or by chromatographic purification. The amine used in this step is either commercially available or can be prepared by methods known to those skilled in the art.

Alternatively, the compounds of the invention wherein $R_9$ is H and $R_{9a}$ is absent, or $R_{9a}$ is H and $R_9$ is absent, may be prepared as follows.

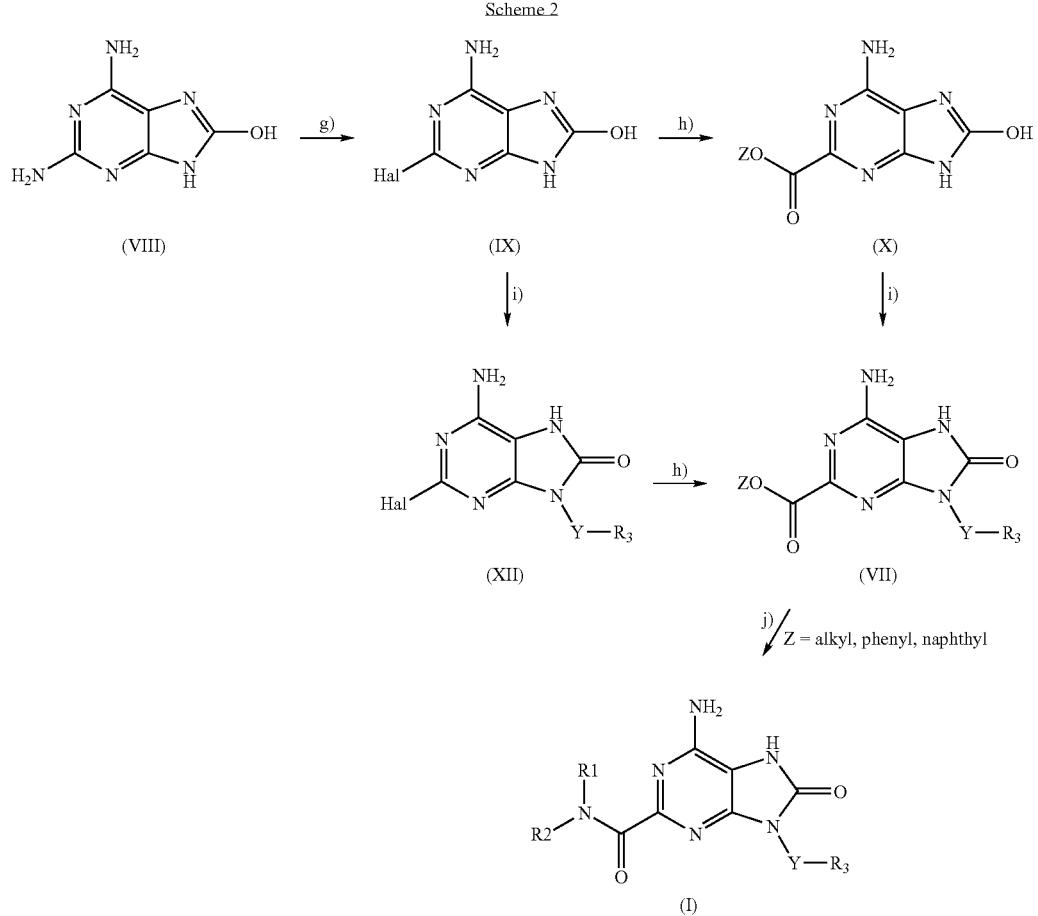

Scheme 2

Z = alkyl, phenyl, naphthyl g) Commercially available 2,6-diamino-8-purinol (VIII) can be halogenated under a variety of conditions (e.g diiodomethane and isoamylnitrite in the presence of a source of copper (I) in a suitable solvent such as THF for Hal=I) to give the halogenated purinol (IX). Methods to perform this transformation are described in *BioOrg. Med. Chem.*, 2001, 9, 2709-2726 and *BioOrg. Med. Chem.*, 2002, 10, 3555-3564, incorporated herein by reference.

h)-i) Compound (IX) can then be carbonylated as described in Scheme 1, step e) to give (X) which can then be alkylated as described in Scheme 1, step a), to give the ester (VII). Alternatively, these steps can be reversed to give (XII) and then (VII).

j) Ester (VII) is then converted to amide (I) as described in Scheme 1, step f)

An alternative synthesis of (XII) is provided in Scheme 3 below.

Scheme 3

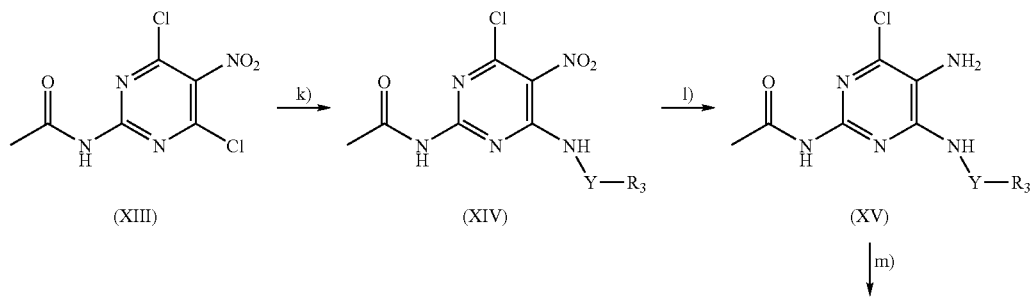

-continued

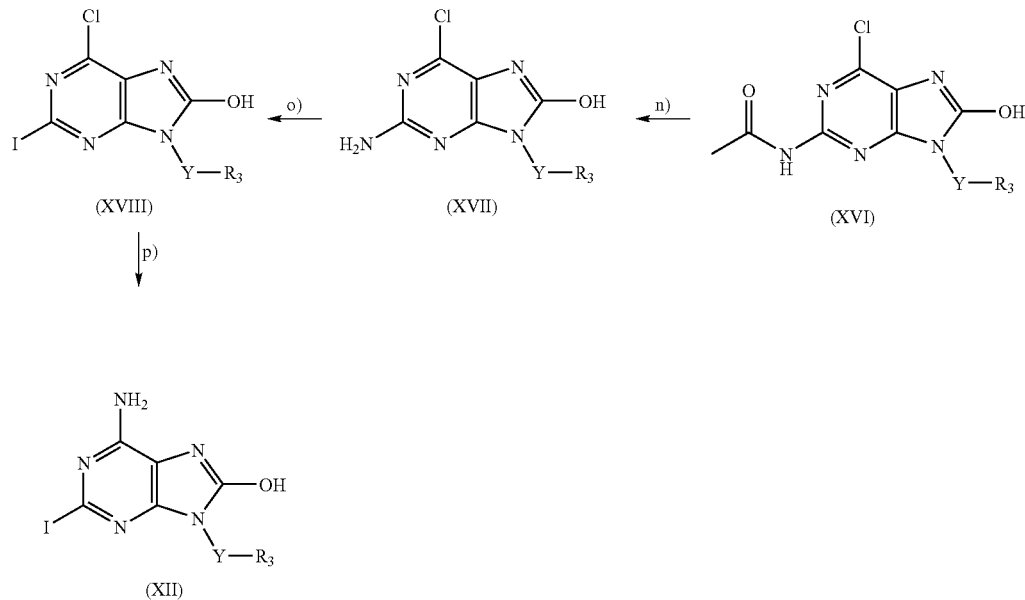

k) (XIII) (prepared according to *J. Org. Chem.*, 1975, 40(21), 3141-3142, incorporated herein by reference) undergoes chlorine displacement with a suitable amine $R_3YNH_2$, either neat or in a suitable solvent such as a lower alcohol (e.g. ethanol, propanol, butanol), optionally in a pressurised reaction vessel. Evaporation of the excess amine and/or solvent under reduced pressure provides the amine (XIV), which can optionally be further purified by recrystallisation from a suitable solvent or by chromatographic purification. Methods for carrying out this transformation are described in *BioOrg. Med. Chem.*, 2001, 9, 2709-2726.

l)-m) The nitro group of (XIV) can then be reduced, for example using Ra—Ni in a suitable solvent such as a lower alcohol (e.g. ethanol, propanol, butanol) under a hydrogen atmosphere, typically 50-200 psi (345-1379 kPa) to give the diaminopyrimidine (XV), which can then be converted to the purinol (XVI) with a suitable source of activated CO, such as carbonyldiimidazole, phosgene, triphosgene or diethyl carbonate.

n)-p) Hydrolysis of the acetamide function of (XVI) gives the 2-aminopurinol (XVII) which can then be halogenated as described in Scheme 2, step g), and the 6-Cl group displaced by ammonia as described in Scheme 1, step b) to give (XII).

A further synthesis of (XII) is provided in Scheme 4 below.

Scheme 4

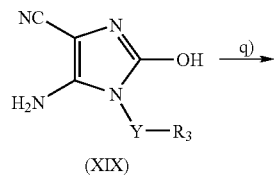

-continued

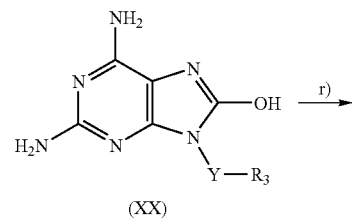

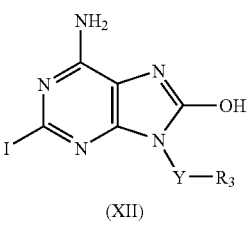

q) (XIX) (prepared according to *Org. BioMol. Chem.*, 2003, 1, 1354-1365, incorporated herein by reference) is converted into diaminopurinol (XX) using a suitable reagent such as guanidine.

r) (XX) is then halogenated to (XII) using the method described in Scheme 2, step g).

Alternatively, the compounds of the invention wherein $R_9$ is H and $R_{9a}$ is absent, or $R_{9a}$ is H and $R_9$ is absent, may be prepared according to Scheme 5 as follows.

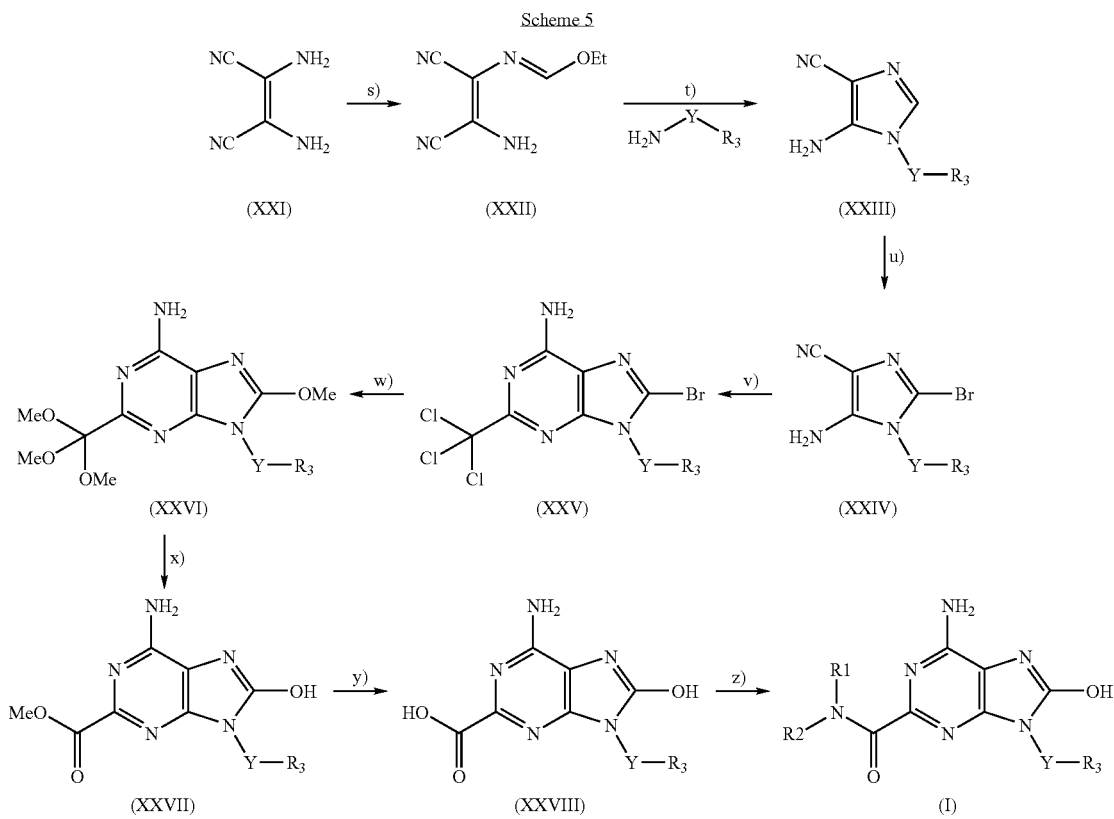

Scheme 5 s), t), u) (XXIV) (prepared according to *Org. BioMol. Chem.*, 2003, 1, 1354-1365, incorporated herein by reference) is prepared from malononitrile in 3 steps. In step t), a range of Y—$R_3$ are introduced to give compound XXIII, which is then brominated in the 2 position to give XXIV, for example using either bromine water or N-bromosuccinimide as the bromine source.

v) XXIV is then reacted with a suitable reagent which produces a C2-substituted trichloromethyl purine derivative XXV. Suitable reagents include trichloromethylacetimidate, trichloroacetonitrile or trichloromethylacetamidine. For an example of the use of the trichloromethyl group as a masked ester see Madding et al., *J. Heterocyclic Chem.*, 1987, 581.

w) XXV is then treated with an alkoxide at elevated temperature which simultaneously converts the trichloromethyl group in an orthoester, and the bromine atom into an alkoxy group to give XXVI. Suitable alkoxides include sodium methoxide, sodium ethoxide and sodium propoxide.

x) XXVI is then treated with a strong acid which simultaneously converts the orthoester into a carboxylic acid ester and the methoxy group of XXVI into a hydroxy group. The ester group of the product XXVII is the same as the orthoester group contained within the starting material XXVI. Suitable acids include mineral acids HCl, HBr, $H_2SO_4$ and $HNO_3$.

y) XXVII is then hydrolysed to produce the carboxylic acid XXVIII. Suitable hydrolysis conditions include strong alkali NaOH, KOH, LiOH or any other suitable ester hydrolysis method known to those skilled in the art. See, for example, those described in 'Protective Groups in Organic Synthesis' by Theodora W Green and Peter G M Wuts, third edition, (John Wiley and Sons, 1999), in particular chapter 7, pages 494-653 ("Protection for the Amino Group"), incorporated herein by reference, which also describes methods for the hydrolysis of such groups.

z) XXVIII is then coupled under amide forming conditions with amines $R_1R_2NH$ to give the product amides 1. Suitable amide forming conditions include the formation of an activated acyl function which reacts with the amine $R_1R_2NH$ to give the product amides. Activated acyl functions can be generated directly in situ from the acid XXVIII with, for example CDI, DCC, BOP, WSCDI, HBTU, T3P, PyBrOP, or any other activating reagent known to those skilled in the art.

Methods to prepare compounds of formula (I) which are prodrugs of other compounds of formula (I) wherein $R_9$ is H and $R_{9a}$ is absent, or $R_{9a}$ is H and $R_9$ is absent, are shown in Scheme 6 below.

Scheme 6

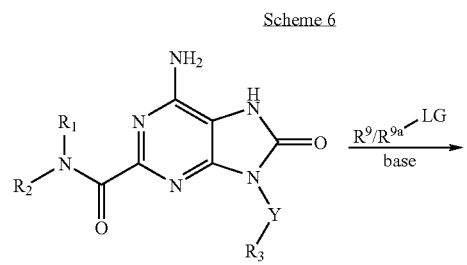

-continued

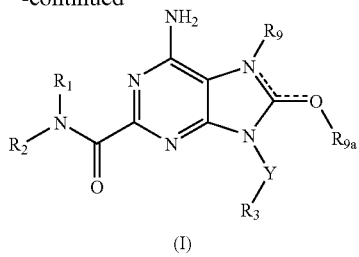

(I)

Reaction of active parent compounds of formula (I) with a reagent which features the group $R_9$ or $R_{9a}$ attached to a suitable leaving group in the presence of a suitable base provides prodrug derivatives of formula (I). Suitable reagents include but are not limited to alkyl halides, acid chlorides, chloroformates and carbamoyl chlorides shown below.

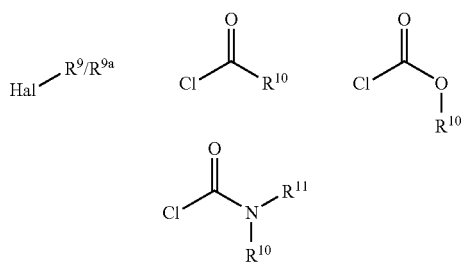

Suitable bases include triethylamine, d isopropylethylamine, potassium carbonate, cesium carbonate, sodium hydride and n-butyllithium. A range of solvents can also be used to effect this transformation, including but not limited to THF, acetonitrile, dimethylformamide, dichloromethane and diethyl ether. The specific choice of both solvent and base can influence the regioselectivity of the alkylation/acylation reaction i.e. whether the reacting group is appended to the O atom ($R_{9a}$) or the N atom ($R_9$). For example, the reaction of a parent molecule with ethyl chloroformate in the presence of triethylamine in DCM will give predominantly O acylation.

It will be appreciated by those skilled in the art that certain of the procedures described in the schemes for the preparation of compounds of formula (I) or intermediates thereto may not be applicable to some of the possible substituents.

It will be further appreciated by those skilled in the art that it may be necessary or desirable to carry out the transformations described in the schemes in a different order from that described, or to modify one or more of the transformations, to provide the desired compound of formula (I).

It will be still further appreciated by those skilled in the art that it may be necessary or desirable at any stage in the synthesis of compounds of formula (I) to protect one or more sensitive groups in the molecule so as to prevent undesirable side reactions. In particular, it may be necessary or desirable to protect amino groups. The protecting groups used in the preparation of compounds of formula (I) may be used in conventional manner. See, for example, those described in 'Protective Groups in Organic Synthesis' by Theodora W Green and Peter G M Wuts, third edition, (John Wiley and Sons, 1999), in particular chapter 7, pages 494-653 ("Protection for the Amino Group"), incorporated herein by reference, which also describes methods for the removal of such groups.

The compounds of formula (I) and their pharmaceutically acceptable salts, solvates and polymorphs are useful because they have pharmacological activity in animals, including humans. More particularly, they are useful in the treatment of a disorder in which the modulation, especially agonism, of TLR7 is implicated.

In one aspect, the compounds of the invention are useful in the treatment of infections caused by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, or respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), a retrovirus (e.g., a lentivirus such as HIV) or a filovirus (e.g., ebola virus or marbug virus).

In another aspect, the compounds of the invention are useful to treat tumors or cancers including but not limited to carcinomas, sarcomas, and leukemias, e.g. squamous cell carcinoma, renal cell carcinoma, Kaposi's sarcoma, melanoma, renal cell carcinoma, myelogeous leukemia, chronic lymphocytic leukemia, multiple myeloma, non-Hodgkin's lymphoma.

In yet another aspect, the compounds of the invention are useful to treat bacterial, fungal, and protozoal infections including but not limited to infections caused by bacteria of the genus Escherichia, Enterobacter, Salmonella, Staphylococcus, Klebsiella, Proteus, Pseudomonas, Streptococcus, Chlamydia; or fungal infections such as candidiasis, aspergillosis, histoplasmosis, cryptococcal meningitis.

In yet another aspect, the compounds of the invention are useful to treat Th2-mediated diseases—(see e.g. Dabbagh et al., Curr Opin Infect Dis 2003, 16: 199-204, incorporated herein by reference), including but not limited to atopic diseases, such as atopic dermatitis or eczema, eosinophilia, asthma, allergy, allergic rhinitis.

In yet another aspect, the compounds of the invention are useful in the treatment of autoimmune diseases.

Accordingly the invention provides a compound of formula (I) or a pharmaceutically acceptable salt, solvate or derivative thereof for use as a medicament.

The invention further provides a compound of formula (I) or a pharmaceutically acceptable salt, solvate or derivative thereof, for the treatment of a disorder in which the modulation of TLR7 receptor is implicated.

The invention further provides a compound of formula (I) or a pharmaceutically acceptable salt, solvate or derivative thereof, for the treatment of a viral infection, tumors or cancer, or a Th2-mediated disease.

The invention further provides the use of a compound of formula (I) or of a pharmaceutically acceptable salt, solvate or derivative thereof, in the manufacture of a medicament for the treatment of a disorder in which the modulation of TLR7 receptor is implicated.

The invention further provides a method of treatment of a disorder or disease in which the modulation of TLR7 receptor is implicated, which comprises administering to a subject in need thereof (e.g., a mammal, including humans) a therapeutically effective amount of a compound of formula (I) or a pharmaceutically acceptable salt, solvate or derivative thereof.

The compounds of the invention may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof. Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995), incorporated herein by reference.

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001), incorporated herein by reference.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980), incorporated herein by reference.

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864, incorporated herein by reference. Details of other suitable release technologies such as high energy dispersions and osmotic and coated particles are to be found in *Pharmaceutical Technology On-line,* 25(2), 1-14, by Verma et al (2001), incorporated herein by reference. The use of chewing gum to achieve controlled release is described in WO 00/35298, incorporated herein by reference.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999), incorporated herein by reference.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an at omiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 μg to 10 mg of the compound of the invention. The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148, incorporated herein by reference.

Inasmuch as it may desirable to administer a compound of the invention in combination with another therapeutic agent, for example, for the purpose of treating a particular disease or condition, it is within the scope of the present invention that two or more pharmaceutical compositions, at least one of which contains a compound of the invention, may conveniently be combined in the form of a kit suitable for coadministration of the compositions.

Thus the kit of the invention comprises two or more separate pharmaceutical compositions, at least one of which contains a compound of formula (I) or a pharmaceutically acceptable salt, solvate or derivative thereof, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, having a weight of about 65 to 70 kg, the total daily dose of a compound of the invention is typically in the range 1 to 10,000 mg, such as 10 to 1,000 mg, for example 25 to 500 mg, depending, of course, on the mode of administration, the age, condition and weight of the patient, and will in any case be at the ultimate discretion of the physician. The total daily dose may be administered in single or divided doses.

Accordingly in another aspect the invention provides a pharmaceutical composition comprising a compound of formula (I) or a pharmaceutically acceptable salt, solvate or derivative thereof together with one or more pharmaceutically acceptable excipients, diluents or carriers.

The advantageous pharmacokinetics of the compounds of the present invention may be demonstrated by using the CACO-2 test. The CACO-2 assay is a widely accepted model for predicting the ability of a given molecule to cross the GI tract.

The test is conducted as described below:

Cell Culture

CACO-2 cells are seeded in 24-well Falcon Multiwell® plates at $4.0 \times 10^4$ cells/well. The cells are grown in culture media consisting of minimum essential medium (Gibco 21090-022) supplemented 20% Fetal Bovine serum, 1% non-essential ammino acids, 2 mM L-glutamine and 2 mM sodium pyruvate. The culture medium is replaced three times every week and the cells are maintained at 37° C., with 5% $CO_2$ and at 90% relative humidity. Permeability studies are conducted when the monolayers are between 15 and 18 days old. Cells were used between passage 23 and 40.

Permeability Studies

Each test compound is prepared as a 10 mM DMSO solution, 62.5 µl of this solution is then added to 25 mL of transport buffer. Nadolol (25 µM) is added to every well as a marker of membrane integrity. These solutions along with transport buffer are then warmed to 37° C. Transport buffer is HBSS (Hank's balanced salt solution) at pH 7.4 or pH 6.5. Before commencing each study, each monolayer is washed three times with HBSS. Transport Buffer with no compound added is placed in each acceptor well, 250 µl on the apical side and 1 mL into the basolateral well. The study is commenced by adding drug solution to each donor well, 250 µl to the apical wells and 1 mL to the basolateral well. Following a two-hour incubation at 37° C. for two hours samples are removed from all wells for LC-MS-MS analysis.

It is desirable that the compounds of present invention are highly selective. In particular it is desirable that the TL7 modulators of the present invention are selective with respect to kinases. Kinases are key mediators of most cellular processes and aberrant activation of kinases is detected in many disease states.

The compounds of formula (I) and their pharmaceutically acceptable salts, solvates and polymorphs may be administered alone or as part of a combination therapy. Thus included within the scope of the present invention are embodiments comprising co-administration of, and compositions which contain, in addition to a compound of the invention, one or more additional therapeutic agents.

In one embodiment, combinations of the present invention include treatment with a compound of formula (I), or a pharmaceutically acceptable salt, solvate or derivative thereof, and one or more additional agents having anti-HCV activity, i.e. agents which can inhibit a target such as, but not limited to, HCV NS5A protein, HCV NS4B protein, HCV polymerase, HCV metalloprotease, HCV serine protease, HCV helicase, p7 protein. Examples of such agents include, but are not limited to, interferons, pegylated interferons (e.g. peginterferon alfa-2a and peginterferon alfa-2b), long-acting interferons (e.g. albumin-interferon alfa), lamivudine, ribavarin, emtricitabine, viramidine, celgosivir, valopicitabine, HCV-086, HCV-796, EMZ702, BILN2061, IDN6566, NM283, SCH 6 and VX-950.

In a further embodiment, combinations of the present invention include treatment with a compound of formula (I), or a pharmaceutically acceptable salt, solvate or derivative thereof, and one or more TLR agonists e.g. against TLR7, TLR8 or TLR9 receptors.

In a further embodiment, combinations of the present invention include treatment of HCV-HIV co-infection with a compound of formula (I), or a pharmaceutically acceptable salt, solvate or derivative thereof, and one or more additional antiviral agents selected from HIV protease inhibitors (PIs), non-nucleoside reverse transcriptase inhibitors (NNRTIs), nucleoside/nucleotide reverse transcriptase inhibitors (NRTIs), CCR5 antagonists, agents which inhibit the interaction of gp120 with CD4, agents which inhibit the entry of HIV into a target cell, integrase inhibitors, prenylation inhibitors and RNaseH inhibitors.

Examples of PIs include, but are not limited to, indinavir, ritonavir, saquinavir, nelfinavir, lopinavir, amprenavir, atazanavir, tipranavir, AG1859 and TMC 114.

Examples of NNRTIs include, but are not limited to, nevirapine, delavirdine, capravirine, efavirenz, rilpivirine, 5-{[3,5-Diethyl-1-(2-hydroxyethyl)-1H-pyrazol-4-yl]oxy}isophthalonitrile or pharmaceutically acceptable salts, solvates or derivatives thereof, 5{[3-Cyclopropyl-1-(2-hydroxyethyl)-5-methyl-1H-pyrazol-4-yl]oxy}isophthalonitrile or pharmaceutically acceptable salts, solvates or derivatives thereof, GW-8248, GW-5634 and TMC125.

Examples of NRTIs include, but are not limited to, zidovudine, didanosine, zalcitabine, stavudine, lamivudine, abacavir, adefovir dipivoxil, tenofovir, emtricitabine and alovudine.

Examples of CCR5 antagonists include, but are not limited to, maraviroc, methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate or pharmaceutically acceptable salts, solvates or derivatives thereof, methyl 3-endo-{8-[(3S)-3-(acetylamino)-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate or pharmaceutically acceptable salts, solvates or derivatives thereof, N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide or derivatives thereof, SCH D, ONO4128, GW873140, AMD-887 and CMPD-167.

Examples of agents which inhibit the interaction of gp120 with CD4 include, but are not limited to, BMS806, BMS488043, 5{(1S)-2-[(2R)-4-Benzoyl-2-methyl-piperazin-1-yl]-1-methyl-2-oxo-ethoxy}4-methoxy-pyridine-2-carboxylic acid methylamide and 4-{(1S)-2-[(2R)-4-Benzoyl-2-methyl-piperazin-1-yl]-1-methyl-2-oxo-ethoxy}3-methoxy-N-methyl-benzamide.

Examples of agents which inhibit the entry of HIV into a target cell include, but are not limited to, enfuviritide, T1249, PRO 542 and PRO 140; an example of integrase inhibitor is L-870,810; examples of prenylation inhibitors include, but are not limited to, HMG CoA reductase inhibitors, such as statins (e.g. atorvastatin).

In yet a further embodiment, combinations of the present invention include treatment with a compound of formula (I), or a pharmaceutically acceptable salt, solvate or derivative thereof, and one or more additional agents such as, but not limited to, antifungals, e.g. fluconazole, fosfluconazole, itraconazole or voriconazole; antibacterials e.g. azithromycin or clarithromycin; interferons, daunorubicin, doxorubicin, and paclitaxel for the treatment of AIDS related Kaposi's sarcoma; and cidofovir, fomivirsen, foscarnet, ganciclovir and valcyte for the treatment of cytomegalovirus (CMV) retinitis.

In yet a further embodiment, combinations of the present invention include treatment with a compound of formula (I), or a pharmaceutically acceptable salt, solvate or derivative thereof, and one or more additional therapeutic agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric 5 presentation of antigen and an adjuvant.

Further combinations for use according to the invention include combination of a compound of formula (I), or a pharmaceutically acceptable salt, solvate or derivative thereof with a CCR1 antagonist, such as BX471; a beta adrenoceptor agonist, such as salmeterol; a corticosteroid agonist, such as fluticasone propionate; a LTD4 antagonist, such as montelukast; a muscarinic antagonist, such as tiotropium bromide; a PDE4 inhibitor, such as cilomilast or roflumilast; a COX-2 inhibitor, such as celecoxib, valdecoxib or rofecoxib; an alpha-2-delta ligand, such as gabapentin or pregabalin; a TNF receptor modulator, such as a TNF-alpha inhibitor (e.g. adalimumab); or an immunosuppressant, such as cyclosporin or a macrolide such as tacrolimus.

There is also included within the scope the present invention, combinations of a compound of formula (I), or a pharmaceutically acceptable salt, solvate or derivative thereof, together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include, but are not limited to, ritonavir, saquinavir or ketoconazole.

In the above-described combinations, the compound of formula (I) or a pharmaceutically acceptable salt, solvate or derivative thereof and other therapeutic agent(s) may be administered, in terms of dosage forms, either separately or in conjunction with each other; and in terms of their time of administration, either simultaneously or sequentially. Thus, the administration of one component agent may be prior to, concurrent with, or subsequent to the administration of the other component agent(s).

Accordingly, in a further aspect the invention provides a pharmaceutical composition comprising a compound of formula (I) or a pharmaceutically acceptable salt, solvate or derivative thereof and one or more additional therapeutic agents.

It is to be appreciated that all references herein to treatment include curative, palliative and prophylactic treatment.

The invention is illustrated by the following Examples and Preparations in which the following further abbreviations may be used:

nBuOH=1-butanol
DMF=Dimethylformamide
DMSO=Dimethylsulfoxide
EtOH=ethanol
EtOAc=ethyl acetate
MeOH=methanol
Me=methyl
Ph=phenyl
Bn=benzyl
c-Hx=cyclohexyl
p-=para
0.88NH$_3$=Concentrated ammonium hydroxide solution, 0.88 SG
dppf=Diphenylphosphinoferrocenyl
NMR=nuclear magnetic resonance
HRMS=high resolution mass spectrometry
LRMS=low resolution mass spectrometry
ES=electrospray
ESI=electrospray ionisation
LCMS=liquid chromatography mass spectrometry
rt=room temperature
h=hour
*denotes carbon atoms to which nitrogen is bonded

EXAMPLE 1

Method A: 6-Amino-9-benzyl-8-oxo-8,9-dihydro-7H-purine-2-carboxylic acid cyclopropylmethyl-amide

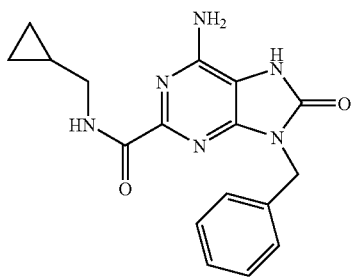

The compound of Preparation 5 (40 mg, 0.13 mmol) was taken up in EtOH (2 mL) and cyclopropylmethylamine (335 µl, 3.8 mmol) in a 5 mL ReactiVial® (Fisher Scientific) and heated at 60° C. for 70 h. A further 335 µl of cyclopropylmethylamine was then added to the vial and heating continued for a further 48 h. The mixture was allowed to cool to rt and was then evaporated to dryness under reduced pressure. The resulting residue was slurried with water (2 mL) and then filtered. The white powder collected was found to be >90% pure product and was used with no further purification (32 mg, 74%). An analytically pure sample was obtained by silica gel chromatography using 2%, then 5%, then 10% MeOH in DCM as the eluent to provide the title compound as a white powder.

$^1$H NMR (d$_6$-DMSO, 400 MHz): 8.34 (br. s, 1H), 7.10-7.36 (m, 5H), 6.88 (br. s, 2H), 4.98 (br. s, 2H), 3.03-3.19 (m, 2H), 0.92-1.05 (m, 1H), 0.30-0.47 (m, 2H), 0.16-0.28 (m, 2H).

EXAMPLE 1

Method B: 6-Amino-9-benzyl-8-oxo-8,9-dihydro-7H-purine-2-carboxylic acid cyclopropylmethyl-amide

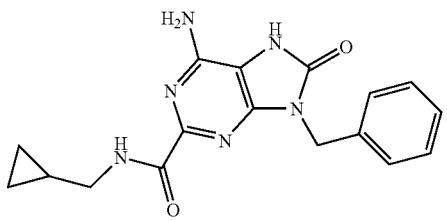

O-benzotriazol-1-yl-tetramethyluronium hexafluorophosphate (48.1 g, 126.8 mmol) was added to a solution of the product of Preparation 12, 6-amino-9-benzyl-8-oxo-8,9-dihydro-7H-purine-2-carboxylic acid (32.88 g, 115.3 mmol) and diisopropylethylamine (40.2 ml, 230.6 mmol) in dimethylacetamide (250 ml) and the reaction mixture stirred at room temperature for 1 hour. Aminomethylcyclopropane (12.5 ml, 144.1 mmol) was added and the reaction mixture stirred at room temperature for a further 20 hours. The reaction mixture was concentrated in vacuo and water added. The resultant precipitate was collected by filtration, azeotroped with toluene and triturated with methanol to yield the title compound.

EXAMPLES 2-11

The following compounds were obtained according to the procedure described above in Example 1, Method A, using the corresponding amine.

TABLE 1

| Example | R$_1$ | R$_2$ | Data ($^1$H NMR) |
|---|---|---|---|
| 2 | CH$_2$CH$_2$OMe | H | 10.42 (br. s, 1H), 8.35 (br. s, 1H), 7.25-7.34 (m, 5H), 6.67 (br. s, 2H), 4.98 (s, 2H), 3.42 (br. m, 4H), 3.26 (s, 3H). |
| 3 | CH$_2$CH$_2$CH$_3$ | H | 10.43 (br. s, 1H), 8.37 (br. s, 1H), 7.24-7.34 (m, 5H), 6.64 (br. s, 2H), 4.99 (s, 2H), 3.15-3.22 (m, 2H), 1.46-1.54 (m, 2H), 0.85-0.88 (m, 3H). |
| 4 | —CH$_2$CH$_2$CH$_2$— | | 7.18-7.30 (m, 5H), 6.62 (s, 2H), 4.92 (s, 2H), 4.30 (t, 2H), 3.94 (t, 2H), 2.10-2.22 (m, 2H). |
| 5 | CH$_3$ | H | 8.23-8.33 (m, 1H), 7.18-7.32 (m, 5H), 6.65-6.88 (m, 2H), 4.98 (s, 2H), 2.75 (d, 2H). |
| 6 | CH$_2$CH$_3$ | H | 8.20-8.34 (m, 2H), 7.18-7.34 (m, 5H), 6.62-6.82 (m, 2H), 4.97 (s, 2H), 3.30 (q, 2H), 1.05 (t, 3H). |

TABLE 1-continued

| Example | R₁ | R₂ | Data (¹H NMR) |
|---|---|---|---|
| 7 | —CH₂CH₂OCH₂CH₂— | | 7.24-7.36 (m, 5H), 5.05 (s, 2H), 3.70-3.74 (m, 4H), 3.55-3.57 (t, 2H), 3.31-3.33 (t, 2H). |
| 8 | —CH₂CH₂N(Me)CH₂CH₂— | | 7.26-7.38 (m, 5H), 5.12 (s, 2H), 3.73-3.80 (m, 2H), 3.59-3.65 (m, 2H), 2.51-2.63 (m, 2H), 2.34-2.42 (m, 2H), 1.28 (s, 3H). |
| 9 | —CH₂CH₂CH₂CH₂— | | 7.14-7.37 (m, 5H), 6.80-6.94 (m, 2H), 4.80-4.94 (m, 2H), 3.00-3.40 (m, 4H), 1.68-1.83 (m, 4H). |
| 10 | CH₂CH₂OH | H | 8.28-8.38 (m, 1H), 7.18-7.37 (m, 5H), 6.70-6.84 (m, 2H), 4.98 (s, 2H), 4.77 (s, 1H), 3.40-3.55 (m, 2H), 3.18-3.40 (m, 2H). |
| 11 | H | H | 7.64-7.81 (m, 1H), 7.18-7.49 (m, 6H), 6.82-6.95 (m, 1H), 4.99 (s, 2H). |

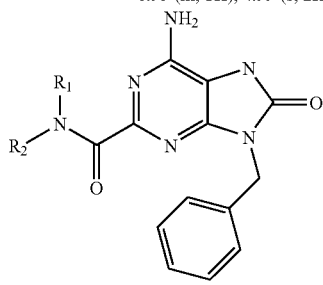

NMR spectra run at 400 MHz in d₆-DMSO except ex. 7 and 8 run in d₄-MeOH

EXAMPLES 12-32

The following compounds were obtained according to the procedure described above in Example 1, Method A, using the corresponding amine.

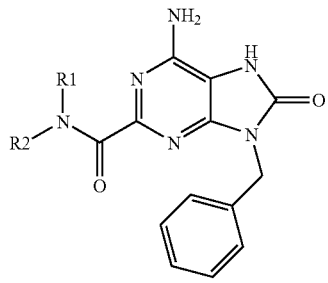

| Example | R₂ | R₁ | LRMS m/z |
|---|---|---|---|
| 12 | | * (isobutyl) | 367 [MH]⁺ |
| 13 | Me | * (cyclopropyl) | 353 [MH]⁺ |
| 14 | H | Bn | |
| 15 | H | * (cyclopropylmethyl) | 353 [MH]⁺ |

-continued

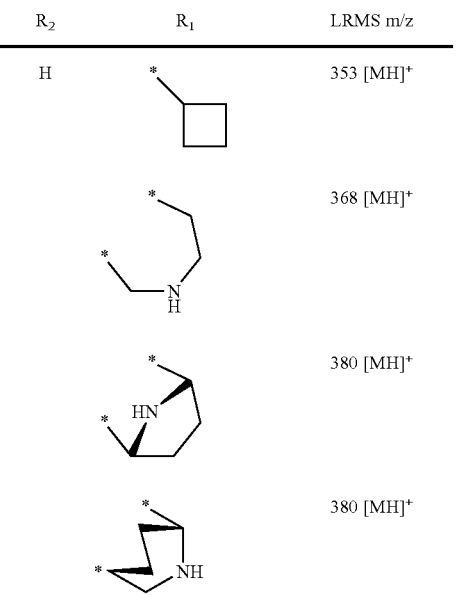

| Example | R₂ | R₁ | LRMS m/z |
|---|---|---|---|
| 16 | H | * (cyclobutyl) | 353 [MH]⁺ |
| 17 | | * (aminoethyl-aminomethyl) | 368 [MH]⁺ |
| 18 | | * (pyrrolidinyl) | 380 [MH]⁺ |
| 19 | | * (pyrrolidinyl) | 380 [MH]⁺ |

-continued

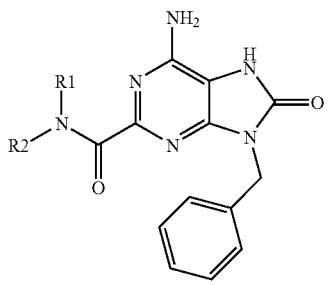

| Example | R₂ | R₁ | LRMS m/z |
|---|---|---|---|
| 20 | | *—C(CH₃)₂—CH₂—NH—* | 382 [MH]⁺ |
| 21 | | *—CH₂—N(Me)—CH₂CH₂CH₃ ( * )* | 382 [MH]⁺ |
| 22 | | N-methylpyrrolidine-3,4-diyl * | 394 [MH]⁺ |
| 23 | Me | N-methylpyrrolidin-3-yl * | 396 [MH]⁺ |
| 24 | H | N-methylpyrrolidin-3-yl * | 368 [MH]⁺ |
| 25 | | pyrrolizidinyl * | 420 [MH]⁺ |
| 26 | | pyrrolidine-2,5-diyl-NH * | 366 [MH]⁺ |
| 27 | | (pyrrolidin-1-yl)methyl * | 394 [MH]⁺ |
| 28 | H | cyclopentyl * | 367 [MH]⁺ |
| 29 | H | cyclopentylethyl * | 381 [MH]⁺ |

-continued

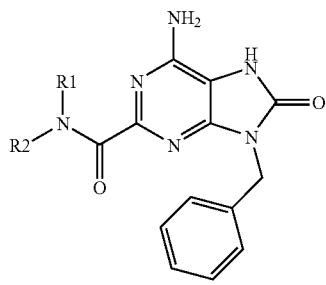

| Example | R₂ | R₁ | LRMS m/z |
|---|---|---|---|
| 30 | H | *—cyclopropyl—CH₂OH (trans) | 369 [MH]⁺ |
| 31 | H | *—cyclopropyl—CH₂OH (cis) | 369 [MH]⁺ |
| 32 | H | *—CH₂—C(O)OH | 343 [MH]⁺ |

EXAMPLES 33-39

The following compounds were obtained using The following compounds were obtained according to the procedure described above in Example 1, Method A, using the product of Preparation 13 and the corresponding amine.

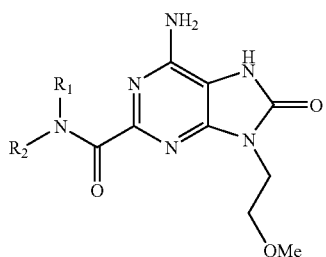

| Example | R₁ | R₂ | Data (¹H NMR/MS) |
|---|---|---|---|
| 33 | Bn | H | 1H NMR (d6-DMSO) δ 8.86 (t, 1H), 7.34-7.30 (m, 5H), 7.26-7.23 (m, 1H), 6.61 (br s, 2H), 4.47 (d, 2H), 3.97 (t, 2H), 3.66 (t, 2H), 3.23 (s, 3H); HRMS for C16H19N6O3 calculated 343.1513, found 343.1511. |
| 34 | CH₂CH₂CH₂CH₃ | H | HRMS for C13H21N6O3 calculated 309.1670, found 309.1668 |
| 36 | Bn | Me | HRMS for C17H21N6O3 calculated 357.1670, found 357.1666 |

-continued

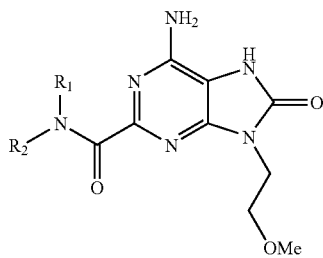

| Example | $R_1$ | $R_2$ | Data ($^1$H NMR/MS) |
|---|---|---|---|
| 37 | —CH$_2$CH$_2$CH$_2$CH$_2$CH$_2$— | | HRMS for C14H21N6O3 calculated 321.1670, found 321.1667 |
| 38 | cyclopentyl* | H | HRMS for C15H23N6O3 calculated 335.1826, found 335.1823 |
| 39 | cyclohexyl* | Me | LRMS (ESI) MH+ 349 m/z |

EXAMPLES 40-220

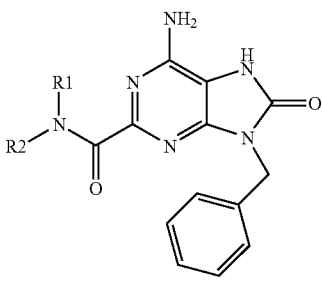

O-benzotriazol-1-yl-N,N,N',N'-tetramethyluronium hexafluorophosphate (55 μmol, 1.1 eq) was added to a solution of the product of Preparation 13, (50 μmol, 1 eq) in dimethylacetamide (0.2M) followed by diisopropylethylamine (115 μmol, 2.3 eq) and the appropriate amine (100 μmol, 2 eq). The reaction mixture was shaken at 40° C. overnight. The solvent was evaporated in a vacuum centrifuge and the residue dissolved in dimethylsulphoxide/water (3:1) to yield the crude product. This material was purified by HPLC on a Phenomenex Luna C18, 5 μm, 30×4.6 mm id column using acetonitrile/0.05% aqueous diethylamine as the mobile phase with a flow rate of 2.5 ml/min. The LC pump gradient timetable is shown below where solvent A=an aqueous solution of 0.05% diethylamine and 5% acetonitrile and B=acetonitrile.

| Time/mins | A % | B % |
|---|---|---|
| 0.00 | 95 | 5 |
| 3.00 | 5 | 95 |
| 3.50 | 95 | 5 |

Retention times are quoted for ELSD detection, which was performed via a Polymerlabs ELSD detection kit at 75° C. and 1.2 bar gas flow. Autosampling is performed via a Gilson Quad Z autosampler using 5 μl injection volume. MS analysis was performed via a Waters ZQ 2000 4 way MUX apparatus in the scan range 160-1000 Da.

| Example Number | $R_2$ | $R_1$ | LCMS/Retention time (min) |
|---|---|---|---|
| 40 | H | *—CH$_2$—pyrrolidinyl | m/z (ES) 382 [MH]$^+$/ 1.90 |
| 41 | H | *—CH$_2$CH$_2$—O—CH$_3$ | m/z (ES) 357 [MH]$^+$/ 1.79 |
| 42 | H | *—CH$_2$-(N-methylpyrrolidin-2-yl) | m/z (ES) 396 [MH]$^+$/ 1.56 |
| 43 | H | *—CH$_2$-(pyridin-2-yl) | m/z (ES) 390 [MH]$^+$/ 1.95 |

-continued
| Example Number | R₂ | R₁ | LCMS/ Retention time (min) |
|---|---|---|---|
| 44 | H | 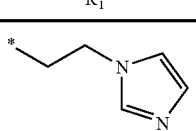 | m/z (ES) 393 [MH]⁺/ 1.63 |
| 45 | H | 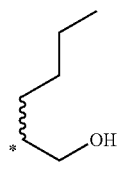 | m/z (ES) 388 [MH]⁺/ 1.97 |
| 46 | H | 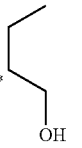 | m/z (ES) 357 [MH]⁺/ 1.69 |
| 47 | H | 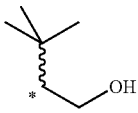 | m/z (ES) 385 [MH]⁺/ 2.33 |
| 48 | Et |  | m/z (ES) 357 [MH]⁺/ 1.59 |
| 49 | | 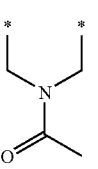 | m/z (ES) 396 [MH]⁺/ 1.66 |
| 50 | | 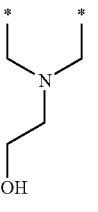 | m/z (ES) 398 [MH]⁺/ 1.85 |
| 51 | | 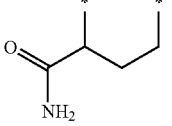 | m/z (ES) 396 [MH]⁺/ 1.51 |
| 52 | | 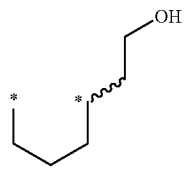 | m/z (ES) 397 [MH]⁺/ 1.79 |
| 53 | H |  | m/z (ES) 341 [MH]⁺/ 2.10 |

-continued
| Example Number | R₂ | R₁ | LCMS/Retention time (min) |
|---|---|---|---|
| 54 | H |  | m/z (ES) 385 [MH]⁺/ 1.93 |
| 55 | H | 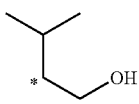 | m/z (ES) 371 [MH]⁺/ 1.80 |
| 56 | H | 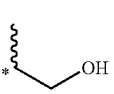 | m/z (ES) 343 [MH]⁺/ 1.58 |
| 57 | H |  | m/z (ES) 355 [MH]⁺/ 2.22 |
| 58 | | 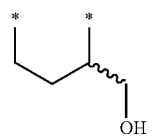 | m/z (ES) 383 [MH]⁺/ 1.62 |
| 59 | iPr |  | m/z (ES) 371 [MH]⁺/ 1.88 |
| 60 | Me | 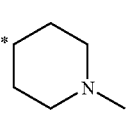 | m/z (ES) 396 [MH]⁺/ 1.82 |
| 61 | | 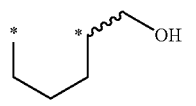 | m/z (ES) 383 [MH]⁺/ 1.75 |
| 62 |  | 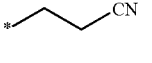 | m/z (ES) 378 [MH]⁺/ 2.07 |
| 63 | nBu |  | m/z (ES) 394 [MH]⁺/ 2.55 |
| 64 | nPr |  | m/z (ES) 371 [MH]⁺/ 1.74 |
| 65 |  | 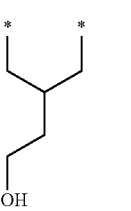 | m/z (ES) 399 [MH]⁺/ 1.98 |
| 66 | | 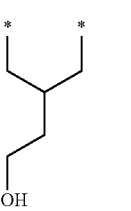 | m/z (ES) 397 [MH]⁺/ 1.80 |

-continued

| Example Number | R₂ | R₁ | LCMS/Retention time (min) |
|---|---|---|---|
| 67 | | *—CH₂CH₂—CH(OH)—* (butyl chain with OH) | m/z (ES) 369 [MH]⁺/ 1.62 |
| 68 | | *—CH₂CH₂—N(Me)—CH₂CH₂—* | m/z (ES) 382 [MH]⁺/ 1.67 |
| 69 | | *—CH₂—CH(OH)—CH₂—* | m/z (ES) 369 [MH]⁺/ 1.84 |
| 70 | H | trans-2-hydroxycyclohexyl | m/z (ES) 383 [MH]⁺/ 1.86 |
| 71 | H | *—CH(Me)—OH | m/z (ES) 343 [MH]⁺/ 1.69 |
| 72 | nPn | *—CH₂OH | m/z (ES) 399 [MH]⁺/ 2.42 |
| 73 | H | *—CH(Et)—OH | m/z (ES) 357 [MH]⁺/ 1.67 |
| 74 | H | *—CH₂CH₂—OH | m/z (ES) 343 [MH]⁺/ 1.67 |
| 75 | H | 3-hydroxycyclohexyl | m/z (ES) 383 [MH]⁺/ 1.60 |
| 76 | | *—CH₂CH₂CH₂—CH(OH)—* | m/z (ES) 383 [MH]⁺/ 2.10 |
| 77 | nPr | *—CH₂—CN | m/z (ES) 380 [MH]⁺/ 2.42 |
| 78 | Me | 3-pyridyl | m/z (ES) 390 [MH]⁺/ 1.69 |
| 79 | | *—CH₂—CH(CH₂OH)—CH₂—* | m/z (ES) 383 [MH]⁺/ 1.52 |

-continued

| Example Number | R₂ | R₁ | LCMS/ Retention time (min) |
|---|---|---|---|
| 80 | | *−CH₂−C(=O)−NH−CH₂−* (cyclic linker with amide) | m/z (ES) 382 [MH]⁺/ 1.59 |
| 81 | | *−CH₂−CH(N(CH₃)₂)−CH₂−* | m/z (ES) 382 [MH]⁺/ 1.99 |
| 82 | Et | *−(CH₂)₃−OH | m/z (ES) 385 [MH]⁺/ 1.70 |
| 83 | H | *−(CH₂)₃−N(CH₃)₂ | m/z (ES) 384 [MH]⁺/ 1.56 |
| 84 | H | *−CH₂−C(CH₃)₂−CH₂−N(CH₃)₂ | m/z (ES) 398 [MH]⁺/ 2.02 |
| 85 | H | *−CH₂−CH₂−CH(CH₃)−CH₂−OH | m/z (ES) 385 [MH]⁺/ 1.97 |
| 86 | H | *−CH(CH₂OH)−CH₂−OH | m/z (ES) 359 [MH]⁺/ 1.76 |
| 87 | Me | *−CH₂−OH | m/z (ES) 343 [MH]⁺/ 1.49 |
| 88 | H | *-cyclohexyl-CH₂OH | m/z (ES) 397 [MH]⁺/ 2.17 |
| 89 | H | *−C(CH₃)₂−CH₂−OH | m/z (ES) 371 [MH]⁺/ 2.25 |
| 90 | | *−CH₂−CH(OEt)−CH₂−* | m/z (ES) 397 [MH]⁺/ 1.89 |
| 91 | | *−CH₂−CH(OMe)−CH₂−* | m/z (ES) 383 [MH]⁺/ 1.74 |

-continued
| Example Number | R₂ | R₁ | LCMS/ Retention time (min) |
|---|---|---|---|
| 92 | H | 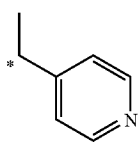 | m/z (ES) 390 [MH]⁺/ 1.92 |
| 93 |  | 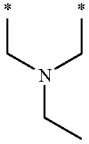 | m/z (ES) 382 [MH]⁺/ 2.03 |
| 94 | H | 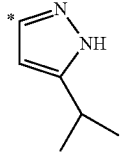 | m/z (ES) 392 [MH]⁺/ 2.22 |
| 95 | H | 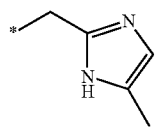 | m/z (ES) 393 [MH]⁺/ 1.97 |
| 96 | H | 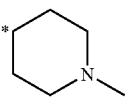 | m/z (ES) 382 [MH]⁺/ 1.52 |
| 97 | H | 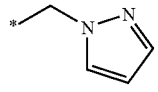 | m/z (ES) 379 [MH]⁺/ 1.89 |
| 98 | H | 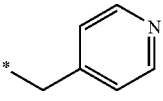 | m/z (ES) 390 [MH]⁺/ 1.70 |
| 99 |  |  | m/z (ES) 378 [MH]⁺/ 1.96 |
| 100 |  | 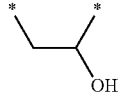 | m/z (ES) 355 [MH]⁺/ 1.88 |
| 101 | H | 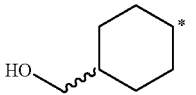 | m/z (ES) 397 [MH]⁺/ 1.67 |
| 102 |  | 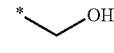 | m/z (ES) 373 [MH]⁺/ 1.75 |
| 103 | H |  | m/z (ES) 362 [MH]⁺/ 1.74 |

-continued

| Example Number | R₂ | R₁ | LCMS/ Retention time (min) |
|---|---|---|---|
| 104 | H | (1H-imidazol-4-yl)methyl | m/z (ES) 379 [MH]⁺/ 1.52 |
| 105 |  | 3-hydroxybutyl (HO-CH(*)-CH₂-CH₂-*) | m/z (ES) 369 [MH]⁺/ 1.79 |
| 106 | H | (1,3-dimethyl-1H-pyrazol-4-yl) | m/z (ES) 393 [MH]⁺/ 1.84 |
| 107 |  | bis(methylene) ether (*-CH(-)-O-CH(-)-*) | m/z (ES) 383 [MH]⁺/ 2.27 |
| 108 |  | 3-methoxybutyl | m/z (ES) 383 [MH]⁺/ 1.80 |
| 109 |  | 3-ethoxybutyl | m/z (ES) 397 [MH]⁺/ 1.93 |
| 110 | H | (1-methyl-1H-pyrazol-4-yl)methyl | m/z (ES) 393 [MH]⁺/ 1.72 |
| 111 | Me | 1,4-dioxan-2-yl | m/z (ES) 399 [MH]⁺/ 1.92 |
| 112 | H | 6-methylpyridin-2-yl | m/z (ES) 390 [MH]⁺/ 2.31 |
| 113 | H | 1,5-dimethyl-1H-pyrazol-3-yl | m/z (ES) 393 [MH]⁺/ 1.70 |
| 114 | H | 1,3-dimethyl-1H-pyrazol-4-yl | m/z (ES) 393 [MH]⁺/ 1.84 |

-continued

| Example Number | R₂ | R₁ | LCMS/ Retention time (min) |
|---|---|---|---|
| 115 | H | 5-methylisoxazol-3-yl (*-attached at 5-position of 3-methylisoxazole) | m/z (ES) 380 [MH]⁺/ 2.25 |
| 116 | H | *-CH₂CH₂CH₂-OH | m/z (ES) 357 [MH]⁺/ 1.57 |
| 117 | H | *-(cyclopentyl)-CH₂OH | m/z (ES) 383 [MH]⁺/ 2.32 |
| 118 | H | *-CH(CH₃)-CH₂OH (isobutyl-OH) | m/z (ES) 357 [MH]⁺/ 1.75 |
| 119 | H | *-(1-ethylpyrrolidin-2-yl) | m/z (ES) 396 [MH]⁺/ 1.67 |
| 120 | Me | 5-(3-methylisoxazolyl) | m/z (ES) 394 [MH]⁺/ 2.08 |
| 121 | Me | 4-methyl-1H-imidazol-2-yl | m/z (ES) 393 [MH]⁺/ 2.00 |
| 122 | Me | 1H-imidazol-2-yl | m/z (ES) 379 [MH]⁺/ 1.56 |
| 123 |  | *-CH₂-NH-C(=O)-CH₂-* | m/z (ES) 368 [MH]⁺/ 1.39 |
| 124 | H | *-CH₂CH₂-O-CH(CH₃)₂ | m/z (ES) 385 [MH]⁺/ 2.44 |
| 125 | H | *-CH₂CH₂-O-CH₃ | m/z (ES) 357 [MH]⁺/ 1.89 |
| 126 | Me | *-CH₂-CN | m/z (ES) 352 [MH]⁺/ 1.70 |
| 127 | Et | *-CH₂-CN | m/z (ES) 366 [MH]⁺/ 2.06 |

-continued
| Example Number | R₂ | R₁ | LCMS/ Retention time (min) |
|---|---|---|---|
| 128 | |  | m/z (ES) 383 [MH]⁺/ 2.28 |
| 129 | Me |  | m/z (ES) 390 [MH]⁺/ 2.17 |
| 130 | | 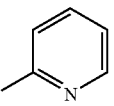 | m/z (ES) 396 [MH]⁺/ 1.50 |
| 131 | | 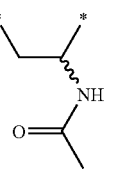 | m/z (ES) 397 [MH]⁺/ 1.85 |
| 132 | | 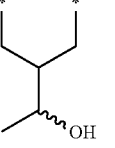 | m/z (ES) 371 [MH]⁺/ 2.33 |
| 133 | H | 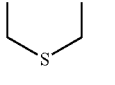 | m/z (ES) 373 [MH]⁺/ 2.02 |
| 134 | | 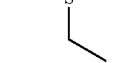 | m/z (ES) 396 [MH]⁺/ 1.72 |
| 135 | H | 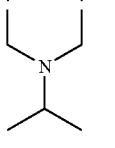 | m/z (ES) 389 [MH]⁺/ 1.78 |
| 136 | | 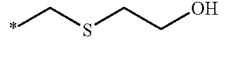 | m/z (ES) 355 [MH]⁺/ 1.85 |
| 137 | | 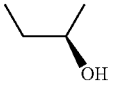 | m/z (ES) 396 [MH]⁺/ 1.47 |
| 138 | | 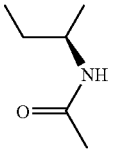 | m/z (ES) 357 [MH]⁺/ 1.88 |

-continued

| Example Number | R₂ | R₁ | LCMS/ Retention time (min) |
|---|---|---|---|
| 139 | H | (isobutyl-CH₂-C(=O)-NH₂ group, attached at *) | m/z (ES) 398 [MH]⁺/ 1.87 |
| 140 | H | (3-hydroxycyclohexyl, attached at *) | m/z (ES) 383 [MH]⁺/ 2.22 |
| 141 | H | (*-CH(OH)-CH₃) | m/z (ES) 343 [MH]⁺/ 1.56 |
| 142 ‡ | Et | (tetrahydrofuran-2-yl, attached at *) | m/z (ES) 397 [MH]⁺/ 1.94 |
| 142A 142B | R enantiomer S enantiomer | | |
| 143 | | (*-CH(CH₃)-N(CH₃)-CH₂-*) | m/z (ES) 382 [MH]⁺/ 1.79 |
| 144 | Me | (1H-pyrazol-3-yl, 5-methyl, attached at *) | m/z (ES) 393 [MH]⁺/ 2.07 |
| 145 | Me | (tetrahydro-2H-pyran-4-yl, attached at *) | m/z (ES) 397 [MH]⁺/ 1.75 |
| 146 | H | (1-methyl-1H-pyrazol-4-yl-ethyl, attached at *) | m/z (ES) 393 [MH]⁺/ 1.75 |
| 147 | H | (1,3-dimethylpyrrolidin-3-yl, attached at *) | m/z (ES) 396 [MH]⁺/ 1.92 |
| 148 | | (*-CH(CH₂OCH₃)-CH₂-CH₂-CH₃, with two * positions) | m/z (ES) 397 [MH]⁺/ 1.94 |

-continued
| Example Number | R₂ | R₁ | LCMS/ Retention time (min) |
|---|---|---|---|
| 149 | | 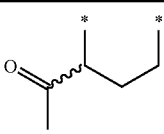 | m/z (ES) 395 [MH]⁺/ 1.82 |
| 150 | Me | 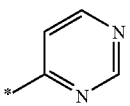 | m/z (ES) 391 [MH]⁺/ 1.62 |
| 151 | Me | 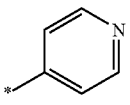 | m/z (ES) 390 [MH]⁺/ 1.69 |
| 152 | H | 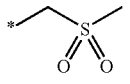 | m/z (ES) 391 [MH]⁺/ 1.81 |
| 153 | H | 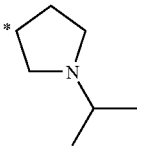 | m/z (ES) 396 [MH]⁺/ 1.97 |
| 154 | H | 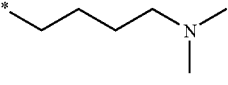 | m/z (ES) 398 [MH]⁺/ 1.48 |
| 155 | | 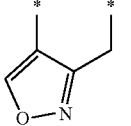 | m/z (ES) 392 [MH]⁺/ 1.82 |
| 156 | | 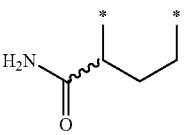 | m/z (ES) 396 [MH]⁺/ 1.66 |
| 157 | H | 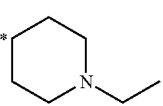 | m/z (ES) 396 [MH]⁺/ 1.56 |
| 158 | | 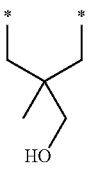 | m/z (ES) 397 [MH]⁺/ 1.86 |
| 159 | H | 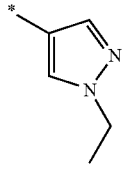 | m/z (ES) 393 [MH]⁺/ 2.15 |

-continued
| Example Number | R₂ | R₁ | LCMS/ Retention time (min) |
|---|---|---|---|
| 160 | H | 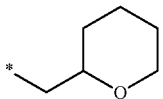 | m/z (ES) 397 [MH]⁺/ 2.04 |
| 161 | H | 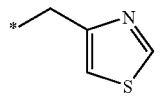 | m/z (ES) 396 [MH]⁺/ 1.82 |
| 162 | H | 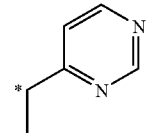 | m/z (ES) 391 [MH]⁺/ 2.10 |
| 163 | H | 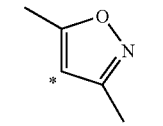 | m/z (ES) 380 [MH]⁺/ 1.87 |
| 164 | | 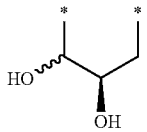 | m/z (ES) 385 [MH]⁺/ 1.35 |
| 165 | | 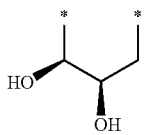 | m/z (ES) 385 [MH]⁺/ 1.62 |
| 166 | H | 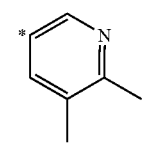 | m/z (ES) 390 [MH]⁺/ 2.38 |
| 167 | Me | 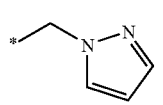 | m/z (ES) 393 [MH]⁺/ 1.74 |
| 168 | nPr | 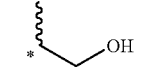 | m/z (ES) 385 [MH]⁺/ 1.85 |
| 169 | nPr | 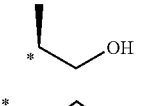 | m/z (ES) 385 [MH]⁺/ 2.06 |
| 170 | H | 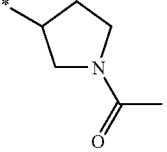 | m/z (ES) 396 [MH]⁺/ 1.91 |
| 171 | | 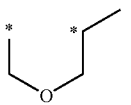 | m/z (ES) 369 [MH]⁺/ 1.74 |

-continued

| Example Number | R₂ | R₁ | LCMS/ Retention time (min) |
|---|---|---|---|
| 172 | | CH₃CH(*)CH₂OH with * branch (2-methylpropane-1,3-diyl with OH) | m/z (ES) 369 [MH]⁺/ 1.88 |
| 173 | | 2,3-bis(hydroxymethyl)butane-2,3-diyl | m/z (ES) 399 [MH]⁺/ 1.55 |
| 174 | H | (cyclopropane-1,2-diyl)methanol | m/z (ES) 369 [MH]⁺/ 1.81 |
| 175 | H | (cyclopropane-1,2-diyl)methanol | m/z (ES) 369 [MH]⁺/ 1.97 |
| 176 | H | 3-(1H-pyrazol-1-yl)propyl | m/z (ES) 393 [MH]⁺/ 1.78 |
| 177 | | 2-(methoxymethyl)butane-1,3-diyl | m/z (ES) 383 [MH]⁺/ 1.94 |
| 178 | | 2-(hydroxymethyl)-2-methylbutane-1,3-diyl | m/z (ES) 397 [MH]⁺/ 1.75 |
| 179 | Me | pyrazin-2-yl | m/z (ES) 391 [MH]⁺/ 1.77 |
| 180 | Me | (1H-pyrazol-4-yl)methyl | m/z (ES) 393 [MH]⁺/ 1.97 |
| 181 | | 2-(hydroxymethyl)-2-methylpropane-1,3-diyl | m/z (ES) 383 [MH]⁺/ 1.55 |

-continued
| Example Number | R₂ | R₁ | LCMS/ Retention time (min) |
|---|---|---|---|
| 182 | H | 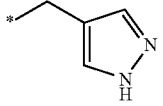 | m/z (ES) 379 [MH]⁺/ 1.98 |
| 183 | H | 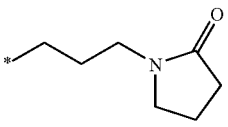 | m/z (ES) 410 [MH]⁺/ 1.62 |
| 184 | H | 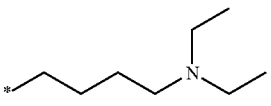 | m/z (ES) 412 [MH]⁺/ 1.75 |
| 185 | | 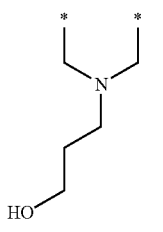 | m/z (ES) 412 [MH]⁺/ 1.78 |
| 186 | | 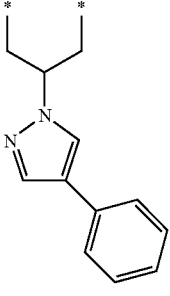 | m/z (ES) 495 [MH]⁺/ 2.80 |
| 187 | | 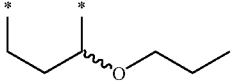 | m/z (ES) 411 [MH]⁺/ 2.33 |
| 188 | Et | 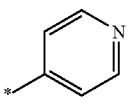 | m/z (ES) 404 [MH]⁺/ 2.15 |
| 189 | H | 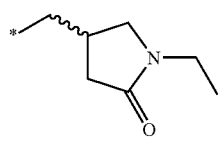 | m/z (ES) 410 [MH]⁺/ 1.64 |
| 190 | | 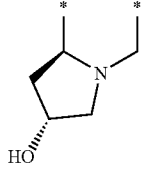 | m/z (ES) 410 [MH]⁺/ 1.53 |

-continued
| Example Number | R₂ | R₁ | LCMS/ Retention time (min) |
|---|---|---|---|
| 191 | H | 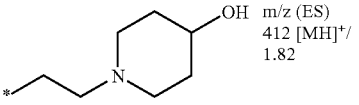 | m/z (ES) 412 [MH]⁺/ 1.82 |
| 192 | Et | 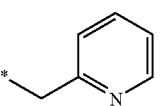 | m/z (ES) 418 [MH]⁺/ 2.29 |
| 193 | | 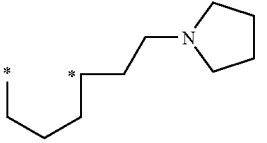 | m/z (ES) 450 [MH]⁺/ 1.65 |
| 194 | H | 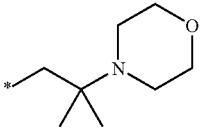 | m/z (ES) 426 [MH]⁺/ 1.89 |
| 196 | H | 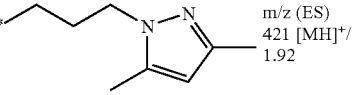 | m/z (ES) 421 [MH]⁺/ 1.92 |
| 197 |  | Bn | m/z (ES) 433 [MH]⁺/ 2.08 |
| 198 | 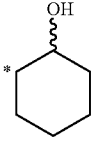 | 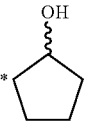 | m/z (ES) 441 [MH]⁺/ 2.19 |
| 199 | 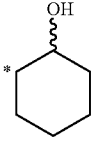 | 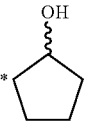 | m/z (ES) 427 [MH]⁺/ 2.23 |
| 200 | | 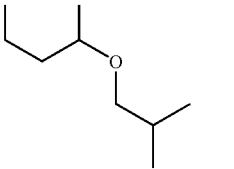 | m/z (ES) 425 [MH]⁺/ 2.35 |
| 201 | H | 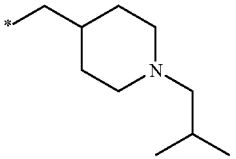 | m/z (ES) 438 [MH]⁺/ 2.11 |

-continued
| Example Number | R₂ | R₁ | LCMS/ Retention time (min) |
|---|---|---|---|
| 202 | H | 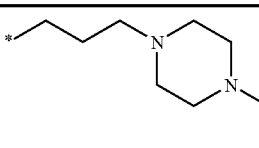 | m/z (ES) 439 [MH]⁺/ 1.50 |
| 203 | H | 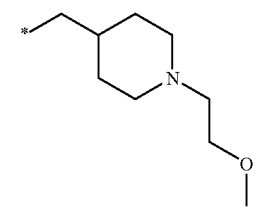 | m/z (ES) 440 [MH]⁺/ 1.58 |
| 204 | H | 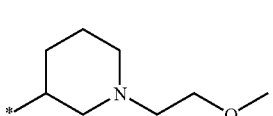 | m/z (ES) 440 [MH]⁺/ 1.77 |
| 205 | H | 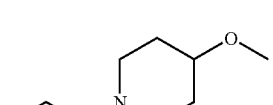 | m/z (ES) 426 [MH]⁺/ 2.05 |
| 206 | Me | 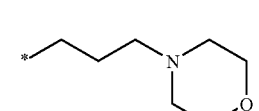 | m/z (ES) 426 [MH]⁺/ 1.60 |
| 207 | H | 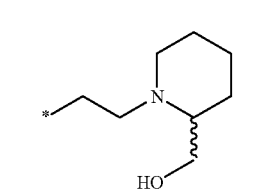 | m/z (ES) 426 [MH]⁺/ 1.56 |
| 208 | H | 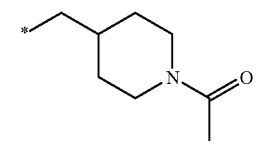 | m/z (ES) 424 [MH]⁺/ 1.80 |
| 209 | Me | 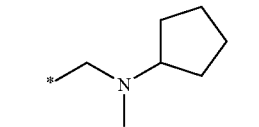 | m/z (ES) 424 [MH]⁺/ 2.19 |
| 210 | Me | Bn | m/z (ES) 389 [MH]⁺/ 2.63 |
| 211 | Me |  | m/z (ES) 337 [MH]⁺/ 1.88 |
| 212 | H | iBu | m/z (ES) 341 [MH]⁺/ 1.89 |

| Example Number | R₂ | R₁ | LCMS/ Retention time (min) |
|---|---|---|---|
| 213 | | (structure) | m/z (ES) 395 [MH]⁺/ 2.60 |
| 214 | H | nBu | m/z (ES) 341 [MH]⁺/ 2.32 |
| 215 | Et | Et | m/z (ES) 341 [MH]⁺/ 1.89 |
| 216 | Me | iPr | m/z (ES) 341 [MH]⁺/ 1.90 |
| 217 | Me | (cyclopropylmethyl structure) | m/z (ES) 393 [MH]⁺/ 2.47 |
| 218 | H | tBu | m/z(ES) 341 [MH]⁺/ 2.32 |
| 219 | Me | nPr | m/z (ES) 341 [MH]⁺/ 1.88 |
| 220 | H | (tetrahydropyran structure) | m/z (ES) 369 [MH]⁺/ 1.69 |

‡ Ex 142 exists as two enantiomers. In addition to the racemate, both enantiomers were also prepared using the corresponding optically pure amine; R enantiomer (Ex 142A) and S enantiomer (Ex 142B)

EXAMPLE 221

6-Amino-9-benzyl-N-(toluylsulfonyl)-8-oxo-8,9-dihydro-7H-purine-2-carboxamide

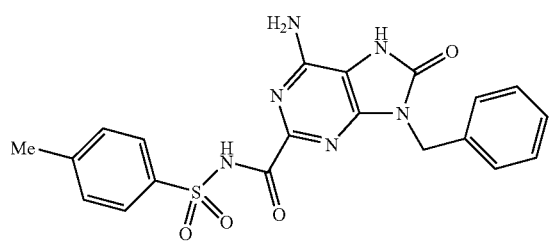

WSCDI (134 mg, 0.70 mmol) was added to a stirred solution of the product of Preparation 13 (100 mg, 0.35 mmol), DMAP (86 mg, 0.70 mmol) and toluylsulfonamide (120 mg, 0.70 mmol) in dimethylacetamide (3 ml) under a nitrogen atmosphere and the mixture stirred at room temperature for 2 days. The reaction mixture was diluted with DCM (10 ml), washed with 2N HCl (5 ml), and the organic layer separated, dried over MgSO4 and evaporated under reduced pressure to a gum which was diluted with 5 ml EtOAc and sonicated to provide a fine off-white solid. This was filtered off to provide the crude product as an off-white solid. This was further purified by preparative reverse phase HPLC, providing the title compound as a pure white solid.

¹H-NMR (DMSO, 400 MHz): δ 019 (s, 3H), 4.99 (s, 2H), 6.70 (s, 2H), 7.19-7.30 (m, 5H), 7.40 (d, 2H), 7.82 (d, 2H), 10.51 (s, 1H), 11.75 (br s, 1H). LRMS m/z (ESI) 439 [MH]⁺.

EXAMPLES 222-228

The following compounds were obtained according to the procedure described above in Example 221, using the corresponding sulphonamide.

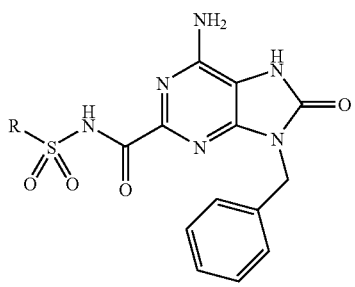

| Example Number | R | LRMS m/z |
|---|---|---|
| 222 | Ph | 425 [MH]+ |
| 223 | p-Cl-Ph | 459 [MH]+ |
| 224 | p-Me-Ph | 439 [MH]+ |
| 225 | p-Ph-Ph | 501 [MH]+ |
| 226 | nBu | 405 [MH]+ |
| 227 | c-Hx | 431 [MH]+ |
| 228 | PhCH₂CH₂ | 453 [MH]+ |

Prodrugs of Example 1

Derivatives which have the potential to increase solubility and/or permeability and hence oral absorption can be prepared from any of the compounds disclosed within this application. The preparation of representative examples is shown below.

EXAMPLE 229

6-Amino-9-benzyl-N-(cyclopropylmethyl)-8-oxo-8,9-dihydro-7H-purine-2-carboxamide ethyl carbonate

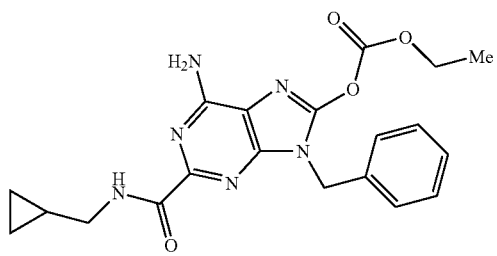

6-Amino-9-benzyl-N-(cyclopropylmethyl)-8-oxo-8,9-dihydro-7H-purine-2-carboxamide (Example 1, 50 mg, 0.15 mmol) was taken up in 2 ml DCM under a nitrogen atmosphere at room temperature and firstly triethylamine (62 µl, 0.44 mmol) and then ethyl chloroformate (28 µl, 0.30 mmol) were added in one portion each and the whole stirred at room temperature for 4 h. The mixture was poured into water (5 ml) and extracted with DCM (3×2 ml). The combined organics were dried over MgSO4 and concentrated in vacuo to a yellow residue which was purified by column chromatography using a gradient of 1:1 DCM:EtOAc→EtOAc as the eluant. Combination and evaporation of the appropriate fractions provided the title compound as a white solid (20 mg).

¹H-NMR (CDCl₃, 400 MHz): δ 0.24-0.27 (m, 2H), 0.53-0.58 (m, 2H), 1.00-1.12 (m, 1H), 1.42 (t, 3H), 3.30 (dd, 2H), 4.48 (q, 2H), 5.07 (s, 2H), 7.21-7.33 (m, 3H), 7.40-7.44 (m, 2H), 7.78 (brs, 1H). LRMS m/z (ESI) 411 [MH]+.

EXAMPLES 230-235

The following compounds were obtained according to the procedure described above in Example 229, using the corresponding chloroformate.

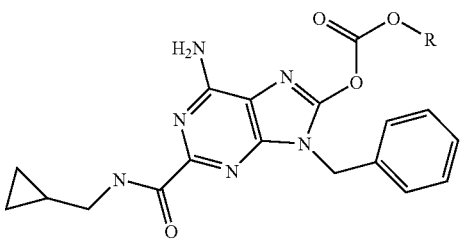

| Example number | R | Data (¹H NMR) |
|---|---|---|
| 230 | Me | ¹H-NMR (CDCl₃, 400 MHz): δ 0.24-0.27 (m, 2H), 0.53-0.58 (m, 2H), 1.00-1.12 (m, 1H), 3.30 (dd, 2H), 4.03 (s, 3H), 5.07 (s, 2H), 7.21-7.33 (m, 3H), 7.40-7.44 (m, 2H), 7.78 (brs, 1H). LRMS m/z (ESI) 397 [MH]+ |
| 231 | nPr | ¹H-NMR (CDCl₃, 400 MHz): δ 0.24-0.27 (m, 2H), 0.53-0.58 (m, 2H), 1.00-1.12 (m, 1H), 1.02 (t, 3H), 1.81 (tq, 2H), 3.30 (dd, 2H), 4.37 (t, 2H), 5.07 (s, 2H), 7.21-7.33 (m, 2H), 7.40-7.44 (m, 2H), 7.78 (brs, 1H). LRMS m/z (ESI) 425 [MH]+ |
| 232 | iPr | ¹H-NMR (CDCl₃, 400 MHz): δ 0.24-0.27 (m, 2H), 0.53-0.58 (m, 2H), 1.00-1.12 (m, 1H), 1.41 (d, 6H), 3.30 (dd, 2H), 5.07 (s, 2H), 5.20 (sept., 1H), 7.21-7.33 (m, 3H), 7.40-7.44 (m, 2H), 7.78 (brs, 1H). LRMS m/z (ESI) 425 [MH]+ |
| 233 | nBu | ¹H-NMR (CDCl₃, 400 MHz): δ 0.24-0.27 (m, 2H), 0.53-0.58 (m, 2H), 0.96 (t, 3H), 1.00-1.12 (m, 1H), 1.47 (tq, 2H), 1.78 (tt, 2H), 3.30 (dd, 2H), 4.41 (t, 2H), 5.07 (s, 2H), 7.21-7.33 (m, 2H), 7.40-7.44 (m, 2H), 7.78 (brs, 1H). LRMS m/z (ESI) 439 |
| 234 | iBu | ¹H-NMR (CDCl₃, 400 MHz): δ 0.24-0.27 (m, 2H), 0.53-0.58 (m, 2H), 1.00-1.12 (m, 1H), 1.04 (d, 6H), 2.10 (sept., 1H), 3.30 (dd, 2H), 4.19 (d, 2H), 5.07 (s, 2H), 7.21-7.33 (m, 2H), 7.40-7.44 (m, 2H), 7.78 (brs, 1H). LRMS m/z (ESI) 439 [MH]+ |

-continued

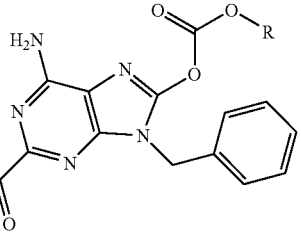

| Example number | R | Data (¹H NMR) |
|---|---|---|
| 235 | ~O~* | ¹H-NMR (CDCl₃, 400 MHz): δ 0.24-0.27 (m, 2H), 0.53-0.58 (m, 2H), 1.00-1.12 (m, 1H), 3.35 (dd, 2H), 3.41 (s, 3H), 3.81 (t, 2H), 4.60 (t, 2H), 5.06 (s, 2H), 7.21-7.38 (m, 3H), 7.45-7.51 (m, 2H), 7.81 (brs, 1H). LRMS m/z (ESI) 441 [MH]⁺ |

EXAMPLE 236

6-Amino-9-benzyl-N-(cyclopropylmethyl)-8-oxo-8,9-dihydro-7H-purine-2-carboxamide propionate ester

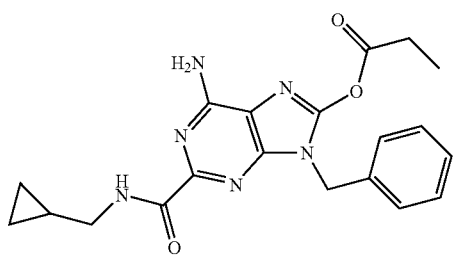

6-Amino-9-benzyl-N-(cyclopropylmethyl)-8-oxo-8,9-dihydro-7H-purine-2-carboxamide (Example 1) was taken up in 3 ml DCM under a nitrogen atmosphere at room temperature and firstly triethylamine (62 μl, 0.44 mmol) and then propionyl chloride (26 μl, 0.30 mmol) were added in one portion each and the whole stirred at room temperature for 16 h. The mixture was poured into water (5 ml) and extracted with DCM (3×2 ml). The combined organics were dried over MgSO4 and concentrated in vacuo to a yellow residue which was purified by column chromatography using a gradient of 1:1 DCM:EtOAc→EtOAc as the eluant. Combination and evaporation of the appropriate fractions provided the title compound as a white solid (26 mg).

¹H-NMR (CDCl₃, 400 MHz): δ 0.19-0.21 (m, 2H), 0.39-0.41 (m, 2H), 0.96-1.01 (m, 1H), 1.08 (t, 3H), 3.10 (3, 4H), 5.01 (s, 2H), 7.21-7.39 (m, 5H), 8.42 (brs, 1H). LRMS m/z (ESI) 395 [MH]⁺.

EXAMPLES 237-238

The following compounds were obtained according to the procedure described above in Example 236, using the corresponding acid chloride.

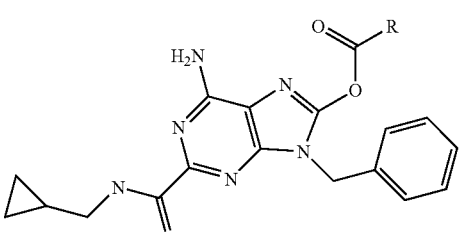

| Example number | R | LRMS m/z |
|---|---|---|
| 237 | Me | 381 [MH]⁺ |
| 238 | Ph | 443 [MH]⁺ |

EXAMPLE 239

6-Amino-9-benzyl-N-(cyclopropylmethyl)-8-oxo-8,9-dihydro-7H-purine-2-carboxamide ethyl carbamate

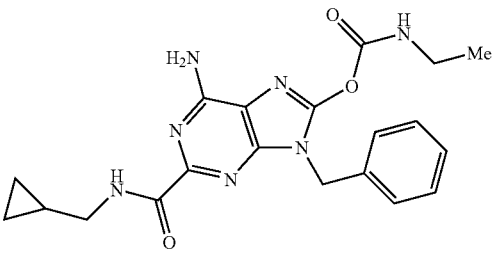

6-Amino-9-benzyl-N-(cyclopropylmethyl)-8-oxo-8,9-dihydro-7H-purine-2-carboxamide (Example 1, 50 mg, 0.15 mmol) was taken up in 2 ml DCM under a nitrogen atmosphere at room temperature and firstly triethylamine (103 μl, 0.74 mmol) and then N-ethyl isocyanate (47 μl, 0.59 mmol) were added in one portion each and the whole stirred at room temperature for 24 h. The mixture was poured into water (5 ml) and extracted with DCM (3×2 ml). The combined organics were dried over MgSO4 and concentrated in vacuo to a yellow residue which was purified by column chromatography using a gradient of 1:1 DCM:EtOAc→EtOAc as the eluant. Combination and evaporation of the appropriate fractions provided the title compound as a white solid (16 mg).

¹H-NMR (CDCl₃, 400 MHz): δ 0.24-0.27 (m, 2H), 0.53-0:58 (m, 2H), 1.00-1.12 (m, 1H), 1.20 (t, 3H) 3.30 (m, 4H), 5.07 (s, 2H), 7.21-7.33 (m, 3H), 7.40-7.44 (m, 2H), 7.78 (brs, 1H), 8.86 (brs, 1H). LRMS m/z (ESI) 410 [MH]⁺.

EXAMPLES 240-244

The following compounds were obtained according to the procedure described above in Example 239, by variation of the isocyanate-component, or by replacement of the isocyanate with an appropriate carbamoyl chloride.

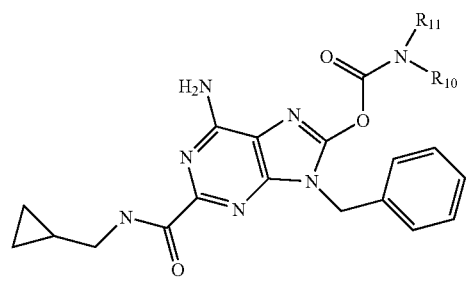

| Example number | R₁₀ | R₁₁ | LRMS m/z |
|---|---|---|---|
| 240 | Me | Me | 410 [MH]⁺ |
| 241 | Et | Et | 438 [MH]⁺ |
| 242 | * ⌐⌐ * | | 450 [MH]⁺ |
| 243 | * ⌐ * | | 436 [MH]⁺ |
| 244 | * ⌐O⌐ * | | 452 [MH]⁺ |

EXAMPLE 244

1H NMR (400 MHz, DMSO) 0.19-0.24 (m, 2H), 0.36-0.45 (m, 2H), 0.94-1.04 (m, 1H), 3.13 (t, 2H), 3.36-3.78 (m, 8H), 5.00 (s, 2H), 6.64 (br. s, 2H), 7.10-7.19 (m, 5H), 8.22 (t, 1H).

EXAMPLE 245

Methyl-6-amino-9-benzyl-4-methoxy-8,9-dihydro-7H-purine-2-carboxylate

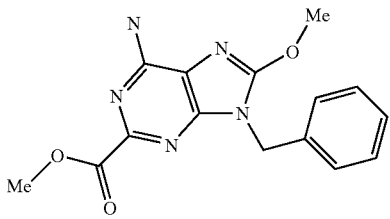

9-Benzyl-8-methoxy-2-(trimethoxymethyl)-9H-purin-6-amine (Preparation 10) (500 mg, 1.39 mmol) was suspended in 2N hydrochloric acid (5 ml) and the reaction mixture stirred at room temperature for 2 hours, during which time a white solid precipitated from the reaction mixture. This was collected by filtration, washed with water and dried, providing the title compound as a white solid (390 mg, 90%).

¹H-NMR (DMSO, 400 MHz): δ 4.0 (s, 3H), 4.18 (s, 3H), 5.21 (s, 2H), 7.21 (s, 2H), 7.26 (m, 5H). LRMS m/z (ESI) 314 [MH]⁺

EXAMPLE 246

6-Amino-9-benzyl-8-methoxy-8,9-dihydro-7H-purine-2-carboxylic acid

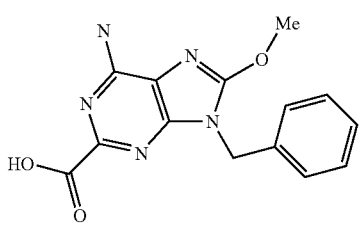

2N Sodium hydroxide (500 μl, 1 mmol) was added to a solution of methyl-6-amino-9-benzyl-8-methoxy-8,9-dihydro-7H-purine-2-carboxylate (Example 245) (100 mg, 0.32 mmol) in methanol (3 ml) and the reaction mixture stirred at room temperature for 2 hours. The solution was acidified to pH 2 with 2N hydrochloric acid and the resultant precipitate collected by filtration and washed with water. The solid was azeotroped with toluene and ether then dried in vacuo to yield the title compound (64 mg, 0.214 mmol).

¹H-NMR (DMSO, 400 MHz): δ 4.08 (s, 3H), 5.19 (s, 2H), 7.10 (s, 2H), 7.19-7.26 (m, 5H). LRMS m/z (ESI) 300 [MH]⁺

EXAMPLE 247

6-Amino-9-benzyl-N-(cyclopropylmethyl)-8-methoxy-8,9-dihydro-7H-purine-2-carboxamide

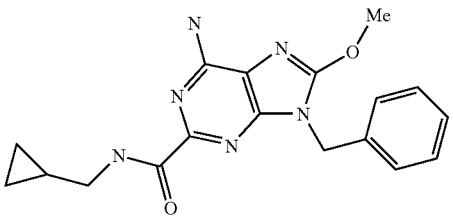

O-benzotriazol-1-yl-tetramethyluronium hexafluorophosphate (89 mg, 0.235 mmol) was added to a solution of 6-amino-9-benzyl-8-methoxy-8,9-dihydro-7H-purine-2-carboxylic acid (Example 246) (64 mg, 0.214 mmol) and diisopropylethylamine (75 μl, 0.428 mmol) in dimethylacetamide (0.5 ml) and the reaction mixture stirred at room temperature for 1 hour. Aminomethylcyclopropane (28 μl, 0.321 mmol) was added and the reaction mixture stirred at room temperature for a further 20 hours. The reaction mixture was concentrated in vacuo and water added. The resultant precipitate was collected by filtration, azeotroped with toluene and triturated with methanol to yield the title compound.

¹H-NMR (CDCl₃, 400 MHz): δ 0.24-0.27 (m, 2H), 0.53-0.58 (m, 2H), 0.97-1.02 (m, 1H), 3.10 (dd, 2H), 4.02 (s, 3H), 5.17 (s, 2H), 7.00 (s, 2H), 7.21-7.33 (m, 5H), 8.38 (brs, 1H). LRMS m/z (ESI) 353 [MH]⁺.

EXAMPLE 248

6-Amino-9-benzyl-N-(cyclopropylmethyl)-8-para-methoxybenzyl-8,9-dihydro-7H-purine-2-carboxamide

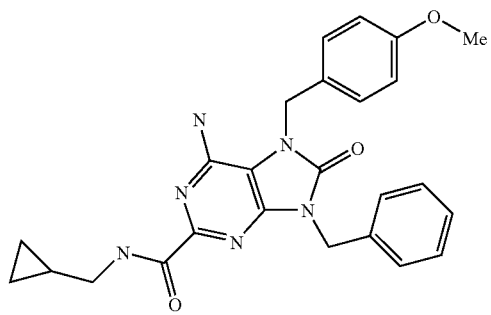

6-Amino-9-benzyl-N-(cyclopropylmethyl)-8-oxo-8,9-dihydro-7H-purine-2-carboxamide (Example 1, 50 mg, 0.15 mmol) was taken up in 3 ml DMA and firstly triethylamine (27 μl, 0.18 mmol) and then para-methoxybenzyl chloride (26 μl, 0.18 mmol) were added in one portion each and the whole stirred and heated to 55° C. for 16 h. The mixture was diluted with ethyl acetate (5 ml) and washed with water (2×3 ml). The combined organics were dried over MgSO4 and concentrated in vacuo to a yellow residue which was purified by column chromatography using a gradient of 100% DCM:→98:2 DCM:MeOH as the eluant. Combination and evaporation of the appropriate fractions provided the title compound as a white solid (19 mg).

$^1$H-NMR (CDCl$_3$, 400 MHz): δ 0.27-0.31 (m, 2H), 0.56-0.58 (m, 2H), 1.01-1.10 (m, 1H), 3.33 (dd, 2H), 3.80 (s, 3H), 5.17 (s, 2H), 5.21 (s, 2H), 6.91 (d, 2H), 7.16 (d, 2H), 7.29-7.39 (m, 3H), 7.50 (m, 2H), 7.85 (brs, 1H). LRMS m/z (ESI) 459 [MH]$^+$.

EXAMPLES 249-250

The following compounds were obtained according to the procedure described above in Example 248, by variation of the alkylating agent.

| Example number | R | LRMS m/z |
|---|---|---|
| 249 | Bn | 429 [MH]$^+$ |
| 250 | * (methyl dioxol-2-one) | 451 [MH]$^+$ |

EXAMPLE 250

1H NMR (400 MHz, DMSO) 0.00-0.04 (m, 2H), 0.20-0.24 (m, 2H), 0.77-0.83 (m, 1H), 1.94 (s, 3H), 2.91-2.94 (t, 2H), 4.84 (s, 2H), 4.94 (s, 2H), 6.73 (br. s, 2H), 7.03-7.11 (m, 5H), 8.19-8.22 (t, 1H).

Preparation 1: 9-Benzyl-2,6-dichloro-9H-purine

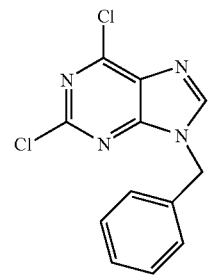

2,6-Dichloro-9H-purine (10.9 g, 60 mmol; purchased from Aldrich Chemical Co.) was dissolved in DMF (200 mL) and potassium carbonate (31.9 g, 230 mmol) added. Benzyl bromide (13.7 mL, 120 mmol) was added in portions and the whole stirred at rt under nitrogen for 16 h. The mixture was filtered through a short plug of Arbocel® and the filtrate was evaporated in vacuo to give a yellow oil of the N7- (more polar) and N9-benzyl (less polar) purines. This oil was purified by silica gel chromatography using 1:2:10 EtOAc:acetone:hexane as eluent to give the title compound as a white solid (9.1 g, 57%).

$^1$H NMR (CDCl$_3$, 400 MHz): 8.03 (s, 1H), 7.37-7.41 (m, 3H), 7.29-7.32 (m, 2H), 5.40 (s, 2H).

Preparation 2: 9-Benzyl-2chloro-9H-purin-6-ylamine

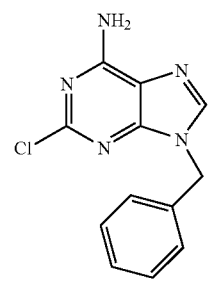

The product from Preparation 1 (10 g, 40 mmol) was suspended in EtOH (60 mL) and 0.88 NH$_3$ solution (70 mL) added. The mixture was heated in a steel pressure vessel at 100° C. for 6 h and then allowed to cool to rt. The reaction mixture was filtered to provide an off-white solid which was washed with water (15 mL) and EtOH (15 mL) and dried under vacuum to provide the title compound as a white solid (8.7 g, 94%).

$^1$H NMR (d$_6$-DMSO, 400 MHz): 8.25 (s, 1H), 7.80 (br. s, 2H), 7.25-7.36 (m, 5H), 5.33 (s, 2H).

Preparation 3: 9-Benzyl-8-bromo-2chloro-9H-purin-6-ylamine

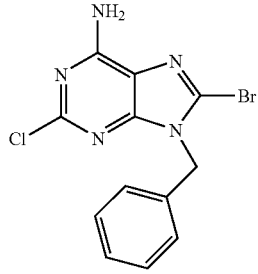

The product from Preparation 2 (3 g, 11.6 mmol) was suspended in AcOH (50 mL) and sodium acetate (1.4 g, 17.3 mmol) and the mixture cooled in an ice bath while bromine (3.6 mL, 69.3 mmol) was added dropwise. After the addition was complete, the mixture was heated at 70° C. under a nitrogen atmosphere for 5 h and then allowed to cool to rt. The mixture was poured onto 50 mL of a 10% aqueous $Na_2S_2O_3$ solution, and the whole reduced in vacuo to approximately 10 mL and then neutralised with 2N NaOH solution. The organics were extracted with DCM (3×150 mL), washed with water (100 mL) and brine (100 mL) and then dried ($MgSO_4$) and evaporated to a yellow solid. Trituration of the solid with ether and filtration provided an off-white solid of the title compound (3.3 g, 85%) which was found to be sufficiently pure to be used with no further purification.

$^1$H NMR ($d_6$-DMSO, 400 MHz): 7.96 (br. s, 2H), 7.28-7.37 (m, 3H), 7.18-7.20 (m, 2H), 5.31 (s, 2H).

Preparation 4: 6-Amino-9-benzyl-2chloro-7,9-dihydro-purin-8-one

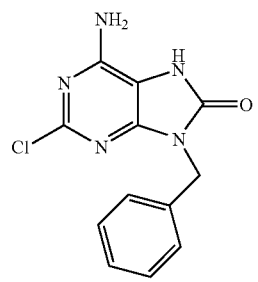

The product from Preparation 3 (2 g, 5.9 mmol) was suspended in 12N HCl (35 mL) and nBuOH (35 mL) and the mixture heated at 100° C. for 7 h and then allowed to cool to rt. The reaction mixture was evaporated to dryness in vacuo, and then partitioned between 2N NaOH (50 mL) and DCM (50 mL). The organic layer was separated and found to contain some unreacted starting material only and was discarded, while the aqueous layer was neutralised with concentrated HCl and the resulting precipitate collected by filtration and washed with EtOAc to give the title compound as an off-white solid (1.5 g, 94%) which was found to be >90% pure and was used with no further purification.

$^1$H NMR ($d_6$-DMSO, 400 MHz): 10.97 (br. m, 1H), 7.20-7.34 (m, 7H), 4.88 (s, 2H).

Preparation 5: 6-Amino-9-benzyl-8-oxo-8,9-dihydro-7H-purin-2-carboxylic acid ethyl ester

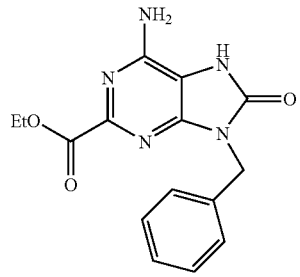

The product from Preparation 4 was suspended in a mixture of EtOH (10 mL) and $Na_2CO_3$ in a steel pressure vessel. $Pd(dppf)_2Cl_2 \cdot DCM$ (30 mg, 0.04 mmol) was added, and the mixture heated at 110° C. under 120 psi (827 kPa) pressure of carbon monoxide for 20 h. After this time, the mixture was allowed to cool to rt and then evaporated under reduced pressure. The resulting residue was chromatographed on silica get using 2%, then 5% MeOH in DCM as the eluent to give the title product as an off-white solid (74 mg, 33%).

$^1$H NMR ($d_6$-DMSO, 400 MHz): 10.54 (br. s, 1H), 7.23-7.33 (m, 5H), 6.76 (br. s, 2H), 4.95 (s, 2H), 4.23-4.29 (q, 2H), 1.25-1.29 (t, 3H).

Preparation 6: Ethyl [(Z)-2-amino-1,2-dicyanovinyl]imidoformate

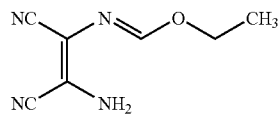

Diaminomaleonitrile (6.0 g, 55.5 mmol) and triethylorthoformate (9.2 ml, 55.5 mmol) were combined in 1,4-dioxane (95 ml) and heated under distillation conditions until 65 ml of 1,4-dioxane/ethanol had been collected. The reaction mixture was cooled to room temperature and the solvent evaporated in vacuo. The residue was purified by column chromatography over silica gel eluting with 0-20% ethyl acetate:pentane. The title compound was obtained as a yellow solid (4.18 g, 25.4 mmol, 46%).

$^1$H-NMR ($CDCl_3$, 400 MHz): δ 1.37 (t, 3H), 4.27 (q, 2H), 4.64 (bs, 2H), 8.00 (s, 1H). LRMS m/z (ESI) 187 [MNa]$^+$

Preparation 7: 5-Amino-1-benzyl-1H-imidazole-4-carbonitrile

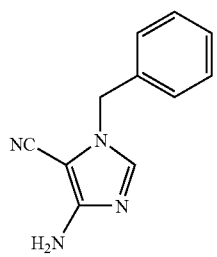

Benzylamine (2.86 ml, 26.3 mmol) was added dropwise to a solution of ethyl [(Z)-2-amino-1,2-dicyanovinyl]imidoformate (4.1 g, 25.0 mmol) and aniline hydrochloride (50 mg) in ethanol (80 ml), stirring at 10° C. and the reaction mixture stirred at room temperature for 18 hours. The reaction mixture was added dropwise to 1M sodium hydroxide (50 ml), stirring at 10° C. and the resultant suspension stirred at room temperature for 18 hours. The solid was collected by filtration, washed with water and dried in vacuo. The title compound was obtained as an off white solid (3.6 g, 18.2 mmol, 73%).

$^1$H-NMR (DMSO, 400 MHz): δ 5.06 (s, 2H), 6.27 (s, 2H), 7.18 (d, 2H), 7.28 (m, 2H), 7.34 (m, 2H). LRMS m/z (ESI) 221 [MNa]$^+$

Preparation 8: 5-Amino-1-benzyl-2-bromo-1H-imidazole-4-carbonitrile

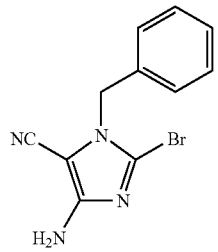

N-bromosuccinimide (3.55 g, 19.9 mmol) was added portionwise to a suspension of 5-amino-1-benzyl-1H-imidazole-4-carbonitrile (3.59 g, 18.1 mmol) in tetrahydrofuran (50 ml) and the reaction mixture stirred at room temperature for 10 minutes. The solvent was evaporated in vacuo and the residue extracted from a saturated aqueous solution of sodium hydrogen carbonate (50 ml) into ethyl acetate (300 ml), dried over magnesium sulphate, filtered and evaporated in vacuo. The crude material was purified by column chromatography over silica gel eluting with 2-3% dichloromethane:methanol. The material was recrystalised from ethyl acetate, then triturated with diethyl ether to yield the title compound as a pink solid (2.7 g, 9.7 mmol, 53%).

$^1$H-NMR (DMSO, 400 MHz): δ 5.10 (s, 2H), 6.71 (s, 2H), 7.09 (m, 2H), 7.28 (m, 1H), 7.36 (m, 2H). LRMS m/z (ESI) 277 [MH]$^+$

Preparation 9: 9-Benzyl-8-bromo-2-(trichloromethyl)-9H-purin-4-amine

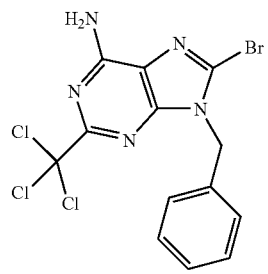

Trichloroacetonitrile (18.36 ml, 183.2 mmol) was added to a suspension of 5-amino-1-benzyl-2-bromo-1H-imidazole-4-carbonitrile (42.3 g, 152.7 mmol) and cesium carbonate (99.5 g, 305.5 mmol) in toluene (500 ml) and the reaction mixture stirred at room temperature for 48 hours. The mixture was poured into water (1000 ml) and extracted into ethyl acetate (1×400 ml, 3×300 ml), dried over magnesium sulphate, filtered and evaporated in vacuo. The residue was suspended in methanol (250 ml) and stirred at room temperature for 18 hours. The resultant solid was collected by filtration and washed with methanol to yield the title compound as an off white solid (54.6 g, 129.7 mmol, 85%).

$^1$H-NMR (DMSO, 400 MHz): δ 5.36 (s, 2H), 7.24 (m, 5H), 7.91 (brs, 2H). LRMS m/z (ESI) 422 [MH]$^+$ Preparation 10: 9-Benzyl-8-methoxy-2-(trimethoxymethyl)-9H-purin-6-amine

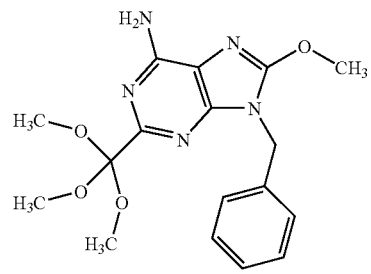

Sodium methoxide (6.92 g, 128.1 mmol) was added portionwise to a suspension of 9-benzyl-8-bromo-2-(trichloromethyl)-9H-purin-6-amine (10.8 g, 25.6 mmol) in methanol (200 ml) and the reaction mixture heated at reflux for 18 hours. The mixture was cooled in ice and quenched with water (100 ml). The methanol was evaporated in vacuo and the residue extracted into ethyl acetate (450 ml), dried over magnesium sulphate, filtered and evaporated in vacuo. The title compound was obtained as a red oil (9.9 g, 27.5 mmol, 100%).

$^1$H-NMR (DMSO, 400 MHz): δ 3.23 (s, 9H), 4.12 (s, 3H), 5.72 (brs, 2H), 7.20 (m, 3H), 7.29 (m, 2H). LRMS m/z (ESI) 360 [MH]$^+$ Preparation 11: Methyl 6-amino-9-benzyl-4-oxo-8,9-dihydro-7H-purine-2-carboxylate

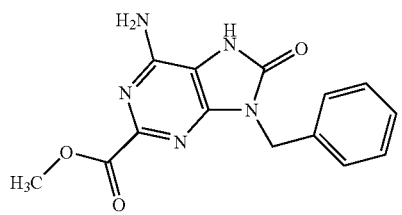

9-Benzyl-8-methoxy-2-(trimethoxymethyl)-9H-purin-6-amine (9.2 g, 25.6 mmol) was suspended in 6N hydrochloric acid (150 ml) and the reaction mixture stirred at room temperature for 60 hours. The mixture was neutralised with 0.880 ammonia and the resultant precipitate collected by filtration and washed with water. The title compound was obtained as a pink solid (7.66 g, 25.6 mmol, 100%).

$^1$H-NMR (DMSO, 400 MHz): δ 3.77 (s, 3H), 4.92 (s, 2H); 670 (brs, 2H), 7.22 (m, 3H), 7.26 (m, 2H). LRMS m/z (ESI) 300 [MH]$^+$ Preparation 12: 6-Amino-9-benzyl-8-oxo-8,9-dihydro-7H-purine-2-carboxylic acid

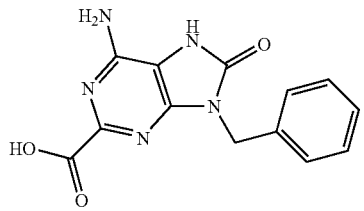

2N Sodium hydroxide (64 ml, 128 mmol) was added to a solution of methyl 6-amino-9-benzyl-8-oxo-8,9-dihydro-7H-purine-2-carboxylate (7.66 g, 25.6 mmol) in methanol (100 ml) and the reaction mixture stirred at room temperature for 2 hours. The solution was acidified to pH 2 with 2N hydrochloric acid and the resultant precipitate collected by filtration and washed with water. The solid was azeotroped with toluene and ether then dried in vacuo to yield the title compound (7.3 g, 25.6 mmol, 100%).

$^1$H-NMR (DMSO, 400 MHz): δ 4.93 (s, 2H), 7.23 (m, 5H), 10.78 (s, 1H). LRMS m/z (ESI) 286 [MH]$^+$

Preparation 13: 6-Amino-9-(2-methoxyethyl)-8-oxo-8,9-dihydro-7H-purine-2-carboxylic acid

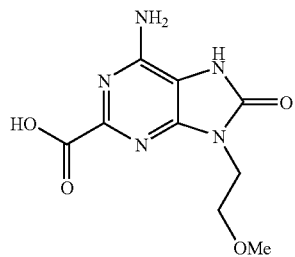

The title compound was prepared in an identical fashion to the product of Preparation 12, but using 2-methoxyethylamine in place of benzylamine.

$^1$H NMR (d6-DMSO) δ 12.76 (br s, 1H), 10.41 (br s, 1H), 6.64 (br s, 2H), 3.94 (t, 2H), 3.65 (t, 2H), 3.23 (s, 3H); HRMS for C9H12N5O4 calculated 254.0884, found 254.0882.

Biological Data

The ability of the compounds of formula (I) and their pharmaceutically acceptable salts, solvates and polymorphs to modulate TLR7 receptor activity is demonstrated by a PB/HCV replicon bioassay as detailed below, in which the following abbreviations may be used:
EMCV: Encephalomyocarditis virus
IRES: Internal ribosmomal entry site
Huh: Huh-7 human hepatoma cell line 7 (parental cells used to generate HCV replicon cell lines)
luc: luciferase
ubi: ubiquitin
neo: neomycin
ET: glutamic acid, threonine (cell culture adaptive mutations in the replicon used in the assay)
RPMI-FCS: Roswell Park Memorial Institute (cell culture medium for PBL)—Foetal Calf Serum
PBL: peripheral blood lymphocytes PBL contain as a subpopulation plasmacytoid dendritic cells which are the natural interferon producing cells during an infection and as such are an excellent model in which to profile interferon inducers. As an extremely sensitive antiviral bioassay, supernatant taken from PBL is assayed for antiviral activity in the HCV replicon system. Antiviral $EC_{50}$ values are defined as the concentration of a test compound applied to PBL that results in a 50% reduction of HCV replicon levels on transfer of a defined amount of PBL culture medium to a HCV replicon containing cell line. Although HCV replicon containing cells are fully responsive to PBL conditioned medium they do not respond directly to known TLR agonists such as Resiquimod and Imiquimod.

The HCV replicon (Huh-5-2[I$_{389}$luc-ubi-neo-NS3-3'/ET]) is an in vitro model of HCV replication in which the luciferase reporter is incorporated into HCV sequences and stably maintained in the human hepatoma cell line Huh-7. The firefly luciferase reporter is expressed as a luciferase-ubiquitin-neomycin phosphotransferase fusion protein which is cleaved by host proteases to release luciferase. The replicon also contains an internal EMCV IRES, which drives translation of HCV NS3-5B polyprotein, which harbour cell culture adapted mutations to permit high cloning efficiency. The luciferase output has been shown to be directly proportional to the level of HCV RNA present in the host cell. Firefly luciferase activity is detected using a Bright-Glo™ Luciferase Assay System manufactured by Promega.

Typically, 1-3 mg of test compound is dissolved in 100% (v/v) DMSO to a final concentration of usually 1, 4 or 10 mM, or higher depending on the starting concentration required in the assay. An initial 3 fold serial dilution series of compounds in 100% DMSO is prepared from stocks. The dilution series is then further diluted 100 fold with complete RPMI—FCS. The final concentration of DMSO in the assay is thus 0.1% and that of the test compound is 1/1000 in the 100% DMSO dilution series.

PBL are prepared seeded at 5×10$^5$/well/90 μl into the previously prepared compound containing assay plates (96 well clear bottomed TC grade) and incubated for 24 h.

LucUbiNeo HCV replicon cells are seeded at 10$^4$/well/90 μl. These are incubated for 24 h. After 24 h 10 μl of medium is transferred from the PBL assay plates to the HCV replicon plates and incubated for a further 48 h.

The compounds of examples 1, 2, 4, 5 and 6 have $EC_{50}$ values of 30 nM, 5 nM, 72 nM, 42 nM and 17 nM, respectively according to the above assay. Examples 1 to 228 all show >50% inhibition at 10 μM.

What is claimed is:
1. A compound selected from the group consisting of:
6-Amino-9-benzyl-8-oxo-8,9-dihydro-7H-purine-2-carboxylic acid cyclopropylmethyl-amide;
6-Amino-9-benzyl-8-oxo-8,9-dihydro-7H-purine-2-carboxylic acid (2-methoxyethyl)-amide;
6-Amino-2-(azetidin-1-carbonyl)-9-benzyl-7,9-dihydro-purine-8-one;
6-Amino-9-benzyl-8-oxo-8,9-dihydro-7H-purine-2-carboxylic acid methylamide;
6-Amino-9-benzyl-8-oxo-8,9-dihydro-7H-purine-2-carboxylic acid ethylamide;
6-amino-9-(2-methoxyethyl)-8-oxo-8,9-dihydro-7H-purine-2-carboxylic acid benzylamide;
6-amino-9-benzyl-2-(thiomorpholine-4-carbonyl)-7,9-dihydro-purine-8-one;
6-amino-9-benzyl-8-oxo-8,9-dihydro-7H-purine-2-carboxylic acid (tetrahydrofuran-2-ylmethyl)amide);
N-(6-amino-9-benzyl-8-oxo-8,9-dihydro-7H-purine-2-carbonyl)-benzenesulfonamide;

Butane-1-sulfonic acid (6-amino-9-benzyl-8-oxo-8,9-dihydro-7H-purine-2-carbonyl)-amide;

Cyclohexanesulfonic acid (6-amino-9-benzyl-8-oxo-8,9-dihydro-7H-purine-2-carbonyl)-amide;

6-Amino-9-benzyl-N-(cyclopropylmethyl)-8-oxo-8,9-dihydro-7H-purine-2-carboxamide ethyl carbonate;

Morpholine-4-carboxylic acid-6-amino-9-benzyl-2-(cyclopropylmethyl-carbamoyl)-9H-purine-8-yl ester;

6-amino-9-benzyl-7-(5-methyl-2-oxo[1,3]dioxol-4-ylmethyl)-8-oxo8,9-dihydro-7H-purine-2-carboxylic acid cyclopropylmethyl amide;

or tautomers thereof and pharmaceutically acceptable salts, solvates or polymorphs of said compounds and tautomers.

2. A compound of formulae (XXV), (XXVI), or (XXVIII):

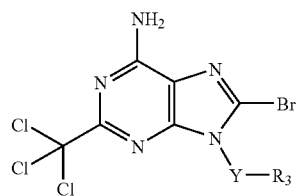
(XXV)

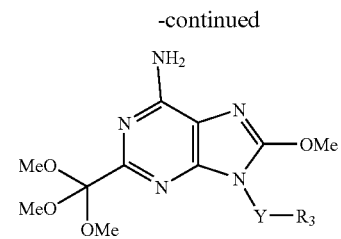
(XXVI)

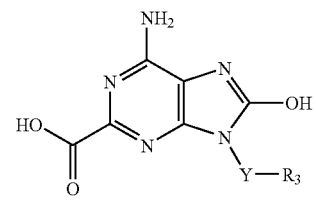
(XXVIII)

wherein $R_3$ is $C_{1-6}$ alkyl; $C_{3-7}$ cycloalkyl; phenyl; naphthyl; or heterocycle; wherein said alkyl, cycloalkyl, phenyl, naphthyl and heterocycle are optionally substituted by 1 to 3 atoms or groups selected from oxo, halogen, $CF_3$, CN, $R_4$, $OR_4$, $NR_4R_5$, $COR_4$, $CO_2R_4$, $S(O)_nR_4$, $S(O)_n NR_4R_5$, $CONR_4R_5$ and $NR_4COR_5$;

Y is a direct bond or a $C_{1-4}$ alkylene;

and Me is methyl.

* * * * *